(12) United States Patent
Phillips et al.

(10) Patent No.: US 9,402,973 B2
(45) Date of Patent: Aug. 2, 2016

(54) CONSTRAINED FLUID DELIVERY DEVICE

(75) Inventors: Frank M. Phillips, Highland Park, IL (US); Kern Singh, Chicago, IL (US)

(73) Assignee: Vital 5, LLC, Logan, UT (US)

( * ) Notice: Subject to any disclaimer, the term of this patent is extended or adjusted under 35 U.S.C. 154(b) by 860 days.

(21) Appl. No.: 12/667,870

(22) PCT Filed: Jul. 2, 2008

(86) PCT No.: PCT/US2008/068998
§ 371 (c)(1),
(2), (4) Date: Feb. 10, 2011

(87) PCT Pub. No.: WO2009/009367
PCT Pub. Date: Jan. 15, 2009

(65) Prior Publication Data
US 2011/0137267 A1    Jun. 9, 2011

Related U.S. Application Data

(60) Provisional application No. 61/066,155, filed on Jul. 6, 2007, provisional application No. 61/031,313, filed on Feb. 25, 2008.

(51) Int. Cl.
*A61M 35/00* (2006.01)
*A61M 25/00* (2006.01)
*A61M 31/00* (2006.01)
*A61M 25/01* (2006.01)

(52) U.S. Cl.
CPC ......... *A61M 25/0068* (2013.01); *A61M 25/007* (2013.01); *A61M 31/00* (2013.01); *A61M 25/0102* (2013.01); *A61M 25/0133* (2013.01); *A61M 2025/0004* (2013.01); *A61M 2025/0057* (2013.01); *A61M 2025/0078* (2013.01); *A61M 2025/0081* (2013.01)

(58) Field of Classification Search
None
See application file for complete search history.

(56) References Cited

U.S. PATENT DOCUMENTS

| 3,572,340 A | 3/1971 | Lloyd et al. |
| 3,823,720 A | 7/1974 | Tribble |

(Continued)

FOREIGN PATENT DOCUMENTS

| JP | 09-108218 A | 4/1997 |
| JP | 11-319103 | 11/1999 |

(Continued)

OTHER PUBLICATIONS

Prior, David V., "Localised Drug Delivery via Collagen-Based Biodegradable Matrices," The Drug Delivery Companies Report Autumn/Winter 2004, pp. 39-42.

(Continued)

*Primary Examiner* — Jason Flick
*Assistant Examiner* — Eric Bryant
(74) *Attorney, Agent, or Firm* — Cary R. Reeves

(57) ABSTRACT

Constrained fluid delivery devices are described that deliver fluid to an anatomical region of a mammal in a controlled release manner where the device comprises an elongate body defining a lumen throughout a portion thereof, a distal end interiorly positionable adjacent the anatomical region of the mammal and a proximal end in communication with an exterior of the mammal. The device also includes a delivery member and one or more withdrawal members. Also provided herein are methods and kits incorporating the fluid delivery device.

11 Claims, 20 Drawing Sheets

(56) References Cited

U.S. PATENT DOCUMENTS

| | | | |
|---|---|---|---|
| 3,854,477 A * | 12/1974 | Smith | 604/512 |
| 3,967,728 A | 7/1976 | Gordon et al. | |
| 4,048,996 A | 9/1977 | Mittleman et al. | |
| 4,364,394 A | 12/1982 | Wilkinson | |
| 4,445,897 A | 5/1984 | Ekbladh et al. | |
| 4,623,329 A | 11/1986 | Drobish | |
| 4,643,716 A | 2/1987 | Drach | |
| 4,692,153 A | 9/1987 | Berlin et al. | |
| D294,639 S | 3/1988 | Croll | |
| 4,786,500 A * | 11/1988 | Wong | 424/422 |
| D300,947 S | 5/1989 | Utas-Sjoberg | |
| 4,925,452 A | 5/1990 | Melinyshyn et al. | |
| 5,034,006 A | 7/1991 | Hosoda et al. | |
| 5,100,395 A | 3/1992 | Rosenberg | |
| 5,120,304 A | 6/1992 | Sasaki et al. | |
| 5,201,723 A | 4/1993 | Quinn | |
| 5,221,255 A | 6/1993 | Mahurkar et al. | |
| 5,234,406 A | 8/1993 | Drasner et al. | |
| 5,318,517 A | 6/1994 | Reiman | |
| 5,320,599 A | 6/1994 | Griep et al. | |
| 5,324,518 A * | 6/1994 | Orth et al. | 424/423 |
| 5,358,494 A * | 10/1994 | Svedman | 604/313 |
| 5,425,723 A | 6/1995 | Wang | |
| 5,433,713 A | 7/1995 | Trotta | |
| 5,458,582 A | 10/1995 | Nakao et al. | |
| 5,458,631 A * | 10/1995 | Xavier | 607/117 |
| 5,523,092 A | 6/1996 | Hanson et al. | |
| 5,533,986 A | 7/1996 | Mottola et al. | |
| 5,545,151 A | 8/1996 | O'Connor | |
| 5,549,603 A * | 8/1996 | Feiring | 604/21 |
| 5,616,121 A | 4/1997 | McKay et al. | |
| 5,647,859 A | 7/1997 | Lampropoulos et al. | |
| 5,647,860 A | 7/1997 | Roth et al. | |
| 5,665,076 A | 9/1997 | Roth et al. | |
| 5,681,274 A | 10/1997 | Perkins et al. | |
| 5,702,372 A | 12/1997 | Nelson | |
| 5,785,678 A | 7/1998 | Griep et al. | |
| 5,873,865 A | 2/1999 | Horzewski et al. | |
| 6,017,323 A | 1/2000 | Chee | |
| 6,117,125 A | 9/2000 | Rothbarth et al. | |
| 6,179,816 B1 | 1/2001 | Mottola et al. | |
| 6,193,704 B1 | 2/2001 | Winters | |
| 6,235,009 B1 | 5/2001 | Skow | |
| 6,325,788 B1 | 12/2001 | McKay | |
| 6,350,253 B1 | 2/2002 | Deniega et al. | |
| 6,514,517 B2 | 2/2003 | Jamiolkowski et al. | |
| 6,524,300 B2 | 2/2003 | Meglin | |
| 6,534,559 B1 | 3/2003 | Vanderlaan et al. | |
| 6,558,686 B1 | 5/2003 | Darouiche | |
| 6,569,839 B1 | 5/2003 | McKay | |
| 6,626,885 B2 | 9/2003 | Massengale | |
| 6,676,643 B2 | 1/2004 | Brushey | |
| 6,689,110 B2 | 2/2004 | Brushey | |
| 6,749,580 B2 * | 6/2004 | Work et al. | 604/29 |
| D499,017 S | 11/2004 | Nestenborg | |
| D499,643 S | 12/2004 | Nestenborg | |
| 6,878,128 B2 | 4/2005 | MacMahon et al. | |
| D505,067 S | 5/2005 | Nestenborg | |
| 6,893,414 B2 | 5/2005 | Goble et al. | |
| 6,921,541 B2 | 7/2005 | Chasin et al. | |
| 7,001,371 B1 | 2/2006 | McLaughlin et al. | |
| 7,004,923 B2 | 2/2006 | Deniega et al. | |
| 7,100,771 B2 | 9/2006 | Massengale et al. | |
| 7,119,062 B1 | 10/2006 | Alvis et al. | |
| 7,186,247 B2 | 3/2007 | Ujhelyi et al. | |
| 7,195,624 B2 | 3/2007 | Lockwood et al. | |
| 7,201,745 B2 | 4/2007 | DiMatteo et al. | |
| 7,232,425 B2 | 6/2007 | Sorenson et al. | |
| 7,282,214 B2 | 10/2007 | Willcox et al. | |
| 7,326,196 B2 | 2/2008 | Olsen et al. | |
| 7,438,711 B2 | 10/2008 | Deniega et al. | |
| 7,452,353 B2 | 11/2008 | Dal Porto et al. | |
| 7,462,165 B2 | 12/2008 | Ding et al. | |
| 7,462,177 B2 | 12/2008 | Brushey | |
| 7,465,291 B2 | 12/2008 | Massengale | |
| 7,510,077 B2 | 3/2009 | Massengale et al. | |
| 7,510,550 B2 | 3/2009 | Deniega et al. | |
| 7,527,609 B2 | 5/2009 | Deniega et al. | |
| 7,534,224 B2 | 5/2009 | Triebes et al. | |
| 7,547,302 B2 | 6/2009 | Porto et al. | |
| 7,569,045 B2 | 8/2009 | Deniega et al. | |
| 7,575,593 B2 | 8/2009 | Rea et al. | |
| D605,757 S | 12/2009 | Sawyer | |
| D605,758 S | 12/2009 | Schwartz et al. | |
| 7,625,337 B2 | 12/2009 | Campbell et al. | |
| 7,699,830 B2 | 4/2010 | Martin | |
| 7,778,852 B2 | 8/2010 | Vasko et al. | |
| 7,780,638 B1 | 8/2010 | Deniega et al. | |
| 7,806,869 B2 | 10/2010 | Nilsson et al. | |
| 7,815,604 B2 | 10/2010 | Massengale et al. | |
| 7,828,790 B2 | 11/2010 | Griffin | |
| 7,854,730 B2 | 12/2010 | Dal Porto et al. | |
| 7,854,732 B2 | 12/2010 | Massengale et al. | |
| 7,942,864 B2 | 5/2011 | Hynes | |
| D640,787 S | 6/2011 | Chia et al. | |
| 7,959,623 B2 | 6/2011 | Massengale | |
| 8,157,759 B2 | 4/2012 | Castillejos | |
| 8,216,176 B2 | 7/2012 | Randolph | |
| 2002/0007204 A1 | 1/2002 | Goode | |
| 2002/0017296 A1 * | 2/2002 | Hickle | 128/203.12 |
| 2002/0082547 A1 * | 6/2002 | Deniega et al. | 604/48 |
| 2002/0177803 A1 | 11/2002 | Chappuis | |
| 2003/0009095 A1 | 1/2003 | Skarda | |
| 2003/0069541 A1 * | 4/2003 | Gillis et al. | 604/164.01 |
| 2003/0069543 A1 | 4/2003 | Bradley, III et al. | |
| 2003/0105511 A1 | 6/2003 | Welsh et al. | |
| 2003/0181864 A1 | 9/2003 | Deniega et al. | |
| 2004/0030281 A1 | 2/2004 | Goble et al. | |
| 2004/0054338 A1 | 3/2004 | Bybordi et al. | |
| 2004/0073194 A1 | 4/2004 | Olsen et al. | |
| 2004/0193262 A1 | 9/2004 | Shadduck | |
| 2005/0085769 A1 | 4/2005 | MacMahon et al. | |
| 2005/0177118 A1 | 8/2005 | Hoganson et al. | |
| 2005/0192638 A1 * | 9/2005 | Gelfand et al. | 607/3 |
| 2005/0272697 A1 | 12/2005 | Herzberg et al. | |
| 2006/0015089 A1 | 1/2006 | Meglin et al. | |
| 2006/0058731 A1 * | 3/2006 | Burnett et al. | 604/29 |
| 2006/0184098 A1 | 8/2006 | Barnitz | |
| 2006/0195059 A1 | 8/2006 | Freyman et al. | |
| 2006/0229573 A1 | 10/2006 | Lamborne | |
| 2006/0229586 A1 | 10/2006 | Faries | |
| 2007/0005004 A1 | 1/2007 | Hynes | |
| 2007/0010786 A1 | 1/2007 | Casey et al. | |
| 2007/0049999 A1 | 3/2007 | Esch et al. | |
| 2007/0073239 A1 | 3/2007 | Skansen et al. | |
| 2007/0106247 A1 | 5/2007 | Burnett et al. | |
| 2007/0118096 A1 | 5/2007 | Smith et al. | |
| 2007/0197959 A1 | 8/2007 | Panotopoulos | |
| 2007/0197970 A1 | 8/2007 | Shen-Gunther | |
| 2007/0219488 A1 | 9/2007 | Francescatti | |
| 2008/0033324 A1 * | 2/2008 | Cornet et al. | 601/6 |
| 2008/0045883 A1 | 2/2008 | Radojicic | |
| 2008/0119802 A1 | 5/2008 | Riesinger | |
| 2009/0182304 A1 | 7/2009 | Deniega et al. | |
| 2009/0184026 A1 | 7/2009 | Massengale et al. | |
| 2010/0000666 A1 | 1/2010 | Deniega et al. | |
| 2010/0222668 A1 | 9/2010 | Dalke et al. | |
| 2011/0137267 A1 | 6/2011 | Phillips et al. | |
| 2012/0330295 A1 | 12/2012 | Manwaring et al. | |

FOREIGN PATENT DOCUMENTS

| | | |
|---|---|---|
| JP | 08-538960 A | 11/2008 |
| WO | 80/01139 A1 | 6/1980 |
| WO | 92/08514 A1 | 5/1992 |
| WO | WO 92/08514 A1 | 5/1992 |
| WO | 95/17918 A1 | 7/1995 |
| WO | WO 95/17918 A1 | 7/1995 |
| WO | 96/30064 A1 | 10/1996 |
| WO | WO 96/30064 A1 | 10/1996 |
| WO | 96/40325 A1 | 12/1996 |
| WO | WO 96/40325 A1 | 12/1996 |
| WO | 97/34655 A1 | 9/1997 |
| WO | WO 97/34655 A1 | 9/1997 |

(56) References Cited

FOREIGN PATENT DOCUMENTS

| WO | 98/18510 | A1 | 5/1998 |
|---|---|---|---|
| WO | WO 98/18510 | A1 | 5/1998 |
| WO | WO 00/15277 | A2 | 3/2000 |
| WO | WO 01/05210 | A2 | 1/2001 |
| WO | WO0132068 | A2 | 5/2001 |
| WO | WO 01/70322 | A1 | 9/2001 |
| WO | 2004/101052 | A3 | 11/2004 |
| WO | WO 2004/101052 | A2 | 11/2004 |
| WO | WO 2004/101052 | A3 | 11/2004 |
| WO | 2005/110521 | A1 | 11/2005 |
| WO | WO 2005/110521 | A1 | 11/2005 |
| WO | 2006/114637 | A2 | 11/2006 |
| WO | 2006/114638 | A2 | 11/2006 |
| WO | 2007/070096 | A1 | 6/2007 |
| WO | WO 2007/070096 | A1 | 6/2007 |
| WO | 2007/142688 | A1 | 12/2007 |
| WO | 2007/143179 | A2 | 12/2007 |
| WO | WO 2007/142688 | A1 | 12/2007 |
| WO | WO 2007/143179 | A2 | 12/2007 |
| WO | 2009/009367 | A2 | 1/2009 |
| WO | 2009/009367 | A3 | 1/2009 |
| WO | WO 2009/009367 | A2 | 1/2009 |
| WO | WO 2009/009367 | A3 | 1/2009 |
| WO | WO2012040311 | A2 | 3/2012 |

OTHER PUBLICATIONS

Innocoll, Inc., "Files US and Irish Patent Applications for its CollaRx® Bupivacaine Implant for the Management of Post-operative Pain," Mar. 29, 2007 10:49:32 AM, from http://www.innocollinc.com/.

Supplementary European Search Report for European patent application No. 08781266.5, dated Jun. 16, 2011, 9 pages.

International Preliminary Report on Patentability, for International application No. PCT/US2008/068998, dated Jan. 12, 2010, 1page.

International Search Report for International application No. PCT/US2008/068998, dated Feb. 25, 2009, 4 pages.

International Search Report for International application No. PCT/US2011/052524, dated Apr. 27, 2012, 6 pages.

English Abstract of JP 11-319103, dated Nov. 24, 1999, 1 pp.

* cited by examiner

US 9,402,973 B2

CONSTRAINED FLUID DELIVERY DEVICE

CROSS-REFERENCE

This application claims the benefit of U.S. Provisional Application Nos. 61/066,155 filed 6 Jul. 2007 and 61/031,313 filed 25 Feb. 2008 which applications are incorporated herein by reference.

BACKGROUND OF THE INVENTION

Pain can have a variety of causes including, for example, resulting from surgical intervention. Patients undergoing surgery often suffer significantly from post-operative pain and have a high likelihood of developing chronic dysaesthesia, causing impairment and sensitivity to touch. Pre-emptive analgesia helps decrease post-operative discomfort by blocking autonomic and somatic reflex responses. Successful management of pain may allow for improved post-operative function, greater patient satisfaction, quicker rehabilitation, and decreased hospitalization. Pre-emptive analgesia may also decrease the likelihood of developing chronic dysaesthesias.

Analgesics may be delivered orally, nasally, intravenously, intramuscularly, and transdermally. Self-administration of intra-venous and intramuscular injections is difficult for patients and the likelihood of compliance is low. Infusion pumps have been used to administer medications; however, complications including infections have been described. Additionally, these devices deliver an unconstrained amount of medication that may be associated with complications as a result of the medication having undesired interactions with local structures, for example, spinal nerves or vital organs.

Other concepts relating to the controlled release of fluids in the body are disclosed in, for example, U.S. Pat. No. 7,119,062 to Alvis for Methods and Compositions for Improved Articular Surgery Using Collagen; U.S. Pat. No. 6,921,541 to Chasin for Formulations and Methods for Providing Prolonged Local Anesthesia; U.S. Pat. No. 7,282,214 to Willcox for Biomedical Devices with Antimicrobial Coatings; U.S. Pat. No. 6,558,686 to Raad for Antimicrobial Coated Medical Implants; U.S. Pat. No. 7,201,745 to DiMatteo for Anti-Infective Central Venous Catheter with Diffusion Barrier Layer; U.S. Pat. No. 6,534,559 to Vanderlaan for Biomedical Devices with Hydrophilic Coatings; and U.S. Pat. No. 6,514,517 to Jamiolkowski for Antimicrobial Coatings fro Medical Devices.

Therefore, it is an object of the present invention to provide methods and apparatuses for delivering medicament in a localized manner to a bodily area.

SUMMARY OF THE INVENTION

The invention described herein includes a device for the delivery of fluid to an anatomical region of a mammal. The device comprises: an elongate body defining a lumen throughout a portion thereof, a distal end interiorly positionable adjacent the anatomical region of the mammal and a proximal end in communication with an exterior of the mammal; a delivery member having an exterior surface; and one or more withdrawal member. The device can be configured to provide biased delivery of fluid. The device can be configured to have more than one elongate body defining more than one lumen. In some cases, the elongate body and the one or more withdrawal members are coated in an antimicrobial agent. The device may further comprise one or more fenestrations at the distal end of the elongate body. The delivery member is typically positioned distal the elongate body and in some embodiments detachable from the elongate body. Additionally, the delivery member can be substantially planar and can be conformable to the anatomical region. Additionally, the portion of the exterior surface of the delivery member is a first side of the planar member. The one or more withdrawal members of the device are typically adjacent to the delivery member. In some cases, the withdrawal member and delivery member are nested along at least a portion of their length. The elongate body in some cases can be steerable by the user, and is capable of being steered by a malleable wire included with the body. The delivery member of the device is typically a porous diffusion member and is capable of being one or more of a bioresorbable matrix, a bioresorbable sponge, a non-resorbable matrix, or a non-resorbable sponge. The delivery device is adapted to be at least partially positioned extradurally, subfascially, subcutaneously, percutaneously, or intramuscularly. Additionally, the device can further comprise a delivery reservoir in communication with the delivery member or a disposal reservoir in communication with the one or more withdrawal members or both a delivery reservoir and a disposal reservoir. The fluid delivered from the delivery reservoir is typically one or more of a medicament, a therapeutic, or saline. The delivery rate of the fluid can be controlled by a sensor in communication with the delivery reservoir and a controller adapted to control a rate at which fluid is delivered. In some cases the elongate body is spiral cut and is adapted and configured to allow fluid flow from the lumen of the elongate body to the exterior of the device. Alternatively, the one or more withdrawal members are spiral cut, where the spiral cut withdrawal member is adapted and configured to provide a channel to draw fluid along its length. The device may further comprise a stylet which is capable of being retractable. A chamber between the elongate body and the delivery member may be present in some embodiments of the device.

Another aspect of the invention is directed to a drug delivery device comprising a delivery tube for delivering a fluid to a local area of tissue from a distal end of the delivery tube; a diffuser in fluid communication with the delivery tube, wherein the diffuser is adapted to be sized to the area of tissue; and a drainage tube for removing fluid from the local area of tissue from a distal end of the drainage tube, wherein the drainage tube is adapted to be introduced to the local area of tissue through the delivery tube lumen. The diffuser can be detachable from the delivery tube. The device can, in some embodiments, further comprise a malleable support structure, wherein the malleable support structure is adapted to support and steer the delivery tube. Additionally, the device can further comprise a fluid reservoir for containing a fluid which can be selected from a medicament, a therapeutic, or saline. In some cases the delivery tube is perforated at the distal end. In some cases, the device can further comprise a drainage tube, wherein the drainage tube is perforated. The delivery tube can also be a spiral cut delivery tube. In some cases, the drainage tube is adjustable relative to the delivery tube. Alternatively, the drainage tube can be fixed relative to the delivery tube and can be entirely encased within the delivery tube. More than one delivery tube is contemplated by the device. Additionally, the delivery tube be coated with any suitable coating wherein the coating is an anti-microbial or antibiotic coating. The withdrawal tube may also be coated with any suitable antimicrobial or antibiotic coating.

In another aspect, provided herein is a device for the delivery of fluid to an anatomical region of a mammal comprising: an elongate body defining a lumen throughout a portion thereof, a distal end interiorly positionable adjacent the anatomical region of the mammal and a proximal end in communication with an exterior of the mammal; and a distally positioned non-tubular delivery member having an exterior surface. The device may provide biased delivery of fluid. One or more elongate bodies defining one or more elongate lumens is further contemplated herein. Furthermore, in some embodiments, the device may further comprise one or more fenestrations at the distal end of the elongate body and a non-tubular delivery member can be positioned distal the elongate body. The non-tubular delivery member is typically planar prior to delivery and a portion of the exterior surface of the delivery member is a first side of the planar membrane. In some cases, one or more withdrawal members are included with the device. The one or more withdrawal members maybe located adjacent to the delivery member. The device may also include one or more elongate bodies. In some cases the one or more withdrawal members and the one or more elongate bodies may be coated with an antimicrobial or antibiotic coating. An alternate embodiment of the device provided herein is a withdrawal member nested within the delivery member along at least a portion of their length. In a further embodiment of the device, the device can be steerable, for example, by including a malleable wire in the device. In some aspects, the non-tubular delivery member is a porous diffusion device. The porous diffusion device may, in some cases, be one or more of a bioresorbable matrix or a bioresorbable sponge. Additionally, the delivery device can be adapted to be at least partially positioned extradurally, subfascially, subcutaneously, percutaneously, or intramuscularly. The device in some embodiments can further comprise a delivery reservoir in communication with the non-tubular delivery member or a disposal reservoir in communication with the one or more withdrawal members or both a delivery member and a disposal reservoir. A sensor in communication with the delivery reservoir and a controller adapted to control a rate at which fluid is delivered may also be included with the device. A spiral cut elongate body is also contemplated by the invention. The spiral cut elongate body is typically adapted and configured to allow fluid to flow from the lumen to the exterior. Alternatively, the withdrawal member can be spiral cut to provide a channel to draw fluid along the length of the withdrawal member. In some cases, the device further comprises a retractable stylet.

In another aspect, provided herein is a device for delivery of fluid to an anatomical region of a mammal comprising: an elongate body defining a lumen throughout a portion thereof, a distal end interiorly positionable adjacent the anatomical region of the mammal and a proximal end in communication with an exterior of the mammal; and a distally positioned delivery member having an exterior surface adapted to deliver fluid from a portion of the exterior surface adjacent the target tissue. The device may provide for biased delivery of fluid to the anatomical region. The device described, in some embodiments, further comprises one or more fenestrations at the distal end of the elongate tubular body. Additionally, the device may further comprise one or more withdrawal elements. The device may also comprise one or more elongate bodies with a delivery member in fluid communication with the distal ends of each of the delivery members. Both the elongate body and the withdrawal member may be coated with an antibiotic or antimicrobial coating. The one or more withdrawal members may be positioned adjacent to the delivery member or members. In some embodiments, the withdrawal member and delivery member are nested along at least a portion of their length. In addition, the device may further comprise a malleable wire for steering the device. The delivery member can, in some embodiments, be positioned the elongate body. The delivery member can be substantially planar prior to delivery and the portion of the exterior surface of the delivery member is a first side of the planar member. In some cases, the delivery member is a porous diffusion device, wherein the porous diffusion device is one or more of a bioresorbable matrix or bioresorbable sponge. The delivery member is further adapted in some cases, to be at least partially positioned extradurally, subfascially, subcutaneously, percutaneously, or intramuscularly. The device in some embodiments may comprise a delivery reservoir in communication with the delivery member. A disposal reservoir in communication with the one or more withdrawal members may also be included in the invention. In a further embodiment of the device, a sensor in communication with the delivery reservoir and a controller adapted to control a rate at which fluid is delivered. In an additional embodiment of the device, the elongate body is a spiral cut elongate body wherein the spiral cut is adapted and configured to allow fluid flow from the lumen to the exterior of the device. Alternatively the withdrawal member can be spiral cut, wherein the spiral cut is adapted and configured to provide a channel to draw fluid along its length. In an additional embodiment, a retractable stylet may be used with the device.

Still another device contemplated is a drug delivery device comprising a delivery tube for delivering fluid to a local area of tissue from a distal end of the delivery tube, and a diffuser in fluid communication with the delivery tube, wherein the diffuser is adapted to be sized to the area of tissue, wherein the fluid is delivered to the local area of tissue through the diffuser. The device may provide, in some embodiments, a biased delivery of fluids. In some embodiments, the diffuser can be adapted to be attachable and detachable from the delivery tube. Alternatively, the diffuser may be integrated with the delivery tube. The diffuser can be a biocompatible matrix, a polymer, a collagenous sponge, a hydrogel, a bioresorbable polymer, a biodegradeable polymer, or any combination thereof. Additionally, a malleable support structure may be included with the device wherein the malleable support structure is adapted to support the delivery tube. The device in some cases may further comprise a fluid reservoir for providing fluid to the diffuser through the delivery tube. The fluid can be a medicament, a therapeutic, or saline. The device can be adapted to be implanted extradurally, subfascially, subcutaneously, percutaneously, or intramuscularly. Additionally, the device may comprise more than one delivery tube. Furthermore, the delivery tube may be perforated at the distal end. In a further embodiment, the device may further comprise a drainage tube, wherein the drainage tube removes fluid from the local area of tissue. The drainage tube may be perforated. The drainage tube may be coupled to the delivery tube. Additionally, the device may further comprise a suction device, wherein the suction device creates suction that is applied to the area of tissue through the drainage tube. In a further embodiment, the device may further comprise a detachable stylet.

A variety of methods are also contemplated. One method includes a method for delivering a fluid to a subject. The method comprises: delivering a distally positioned delivery member adjacent a target tissue within a mammalian body; delivering fluid to the delivery member via an elongate body; and withdrawing excess delivered fluid adjacent the target tissue via a withdrawal member. The target tissue can be tissue selected from spinal dura mater, skin, subcutaneous tissue, paraspinal muscle, bone, ligaments, facia, and neural elements. The method can further comprise the step of detaching the delivery member from the elongate body. Additionally, the method may include the step of applying a vacuum to the delivery member. The distal portion of the delivery member can be removed after a therapeutic length of time has elapsed. The fluid used could be a medicament comprising one or more of anesthesia, anti-inflammatories, analgesics, anti-catabolites, growth factors, hormones, viral or recombinant proteins, or any other fluid suitable for being administered. The step of replacing the first reservoir with a second reservoir may be used. A first fluid can be delivered through via the first reservoir and a second fluid can be delivered via the second reservoir. The method can further include the step of positioning the device extradurally, subfascially, subcutaneously, percutaneously, or intramuscularly. Additionally, the delivery of fluids can be controlled or adjusted in response to measuring a target parameter of the patient.

A variety of kits are also contemplated. For example a kit for administering fluid can be provided comprising, for example, (a) an elongate body defining a lumen throughout a portion thereof, a distal end interiorly positionable adjacent the anatomical region of the mammal and a proximal end in communication with an exterior of the mammal; (b) a delivery member having an exterior surface, and (c) a withdrawal member. The kit may further comprise a delivery reservoir in communication with the delivery member. A sensor in communication with the delivery reservoir and a controller adapted to control the rate at which fluid is delivered may also be included. Additionally, the kit may further comprise a disposal reservoir in communication with the withdrawal member.

A drug delivery kit is also contemplated. A drug delivery kit could comprise, for example, (a) a delivery tube for delivering a fluid to a local area of tissue, (b) a diffuser in fluid communication with the delivery tube, wherein the diffuser is adapted to be sized to the area of tissue, and (c) a drainage tube for removing fluid from the local area of tissue. The kit may further comprise a fluid reservoir. Additionally, the kit may include a suction device, wherein the suction device applies reduced pressure to the area of tissue through the drainage tube.

A kit comprising a device for delivering fluid to an anatomical region of a mammal is also contemplated comprising, for example, (a) an elongate body defining a lumen throughout a portion thereof, a distal end interiorly positionable adjacent the anatomical region of the mammal and a proximal end in communication with an exterior of the mammal, and (b) a distally positioned non-tubular delivery member having an exterior surface. In some embodiments, the kit may include a withdrawal member and may include more than one withdrawal members. A delivery reservoir may be included in the kit wherein the delivery reservoir is in communication with the non-tubular delivery member. Additionally a disposal reservoir in communication with the one or more withdrawal members may be included in the kit.

A kit comprising a device for delivering fluid to an anatomical region of a mammal can alternatively comprise (a) an elongate body defining a lumen throughout a portion thereof, a distal end interiorly positionable adjacent the anatomical region of the mammal and a proximal end in communication with an exterior of the mammal, and (b) a distally positioned delivery member having an exterior surface adapted to deliver fluid from a portion of the exterior surface adjacent the target tissue. In some cases, the kit may further comprise one or more withdrawal members. The kit may further comprise a delivery reservoir in communication with the delivery member. A sensor in communication with the delivery reservoir and a controller adapted to control the rate at which fluid is delivered may also be included. Additionally, the kit may further comprise a disposal reservoir in communication with the withdrawal member.

In an alternative embodiment of a drug delivery kit, the kit may comprise (a) a delivery tube for delivering a fluid to a local area of tissue, and (b) a diffuser in fluid communication with the delivery tube, wherein the diffuser is adapted to be sized to the area of tissue, wherein the fluid is delivered to the local area of tissue through the diffuser. The kit in some embodiments can also include a fluid reservoir for providing fluid to the diffuser through the delivery tube. Additionally, a drainage tube may be included in the kit, wherein the drainage tube is used to remove fluid from the local area of tissue.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

The present invention provides constrained delivery systems for treating pain associated with surgical procedures in a mammal. Typically, the invention can be used to treat post-operative pain suffered by patients who have undergone spinal surgery. The device can be configured to deliver a substance, such as a medicament, in a controlled, localized fashion and substantially prevents the substance from contacting or negatively impacting other areas of the body that may be impaired by the medicament or might be impaired by exposure to an excessive or uncontrolled amount of the substance. The device does so through the use of a delivery member that controls the rate and volume of fluid administered to the anatomical region. Alternatively, the invention may be used to treat post-operative pain in other anatomical regions, such as intra-cranial, thoracic, abdomino-pelvic, or articular areas where it is desirable to constrain the delivery of medicament to prevent the medicament from contacting and affecting vital structures in proximity to the implantation site of the device. The anatomical regions of interest can include spinal dura matter, skin, subcutaneous tissue, paraspinal muscle, bone, ligaments, facia, and neural elements. Additionally, the device can be used to treat the areas surrounding vascular structures, cardiac structures and neural structures. Although the devices, systems and methods described herein have a wide range of application, for purposes of illustration, the devices, systems and methods will be described with respect to a human spine. As will be appreciated by those skilled in the art, excessive exposure by the spine to an analgesic can cause temporary paralysis, which would be an undesirable side effect to any effort at pain management.

The spinal cord is a collection of neurons that travels within the vertebral column and is an extension of the central nervous system. The spinal cord extends from the brain and is enclosed in and protected by the bony vertebral column. In delivering pain relieving medicaments directly to the spinal area, conventional methods suffer the drawback of the medicament interfering with nerves within the spinal cord and with surrounding peripheral nerves. Uncontrolled delivery of analgesia may cause an unwanted diffusion of medication to surrounding vital structures such as nerves, with a resultant loss of sensation and motor function. This effect is often temporary but may last as long as the treatment.

Figure 1A:
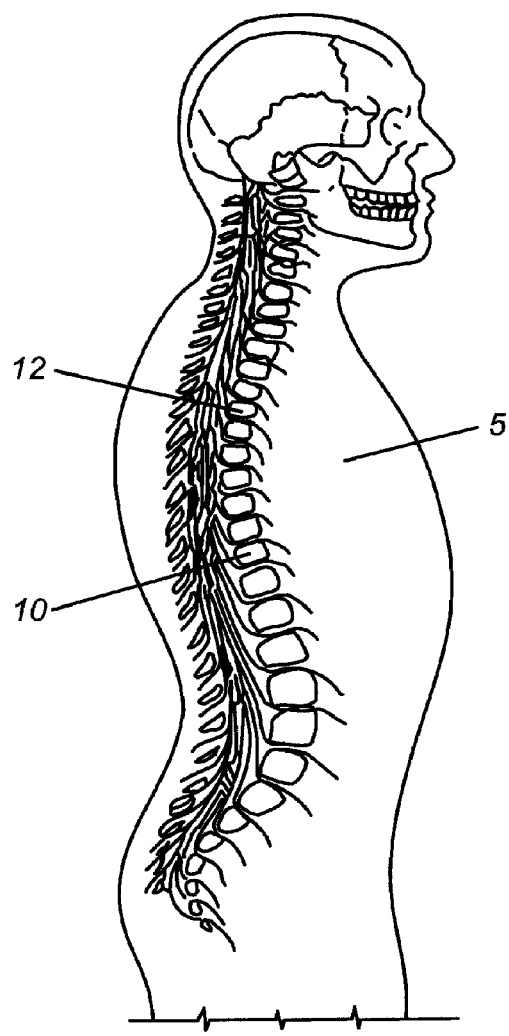
FIG. 1A is a lateral view of the spinal column.

A body cavity 5 with spinal column is shown in FIG. 1A. The devices of the invention are designed to interact with the human spinal column 10, as shown in FIG. 1A, which is comprises of a series of thirty-three stacked vertebrae 12 divided into five regions. The cervical region includes seven vertebrae, known as C1-C7. The thoracic region includes twelve vertebrae, known as T1-T12. The lumbar region contains five vertebrae, known as L1-L5. The sacral region is comprised of five fused vertebrae, known as S1-S5, while the coccygeal region contains four fused vertebrae, known as Co1-Cu4.

Figure 1B:
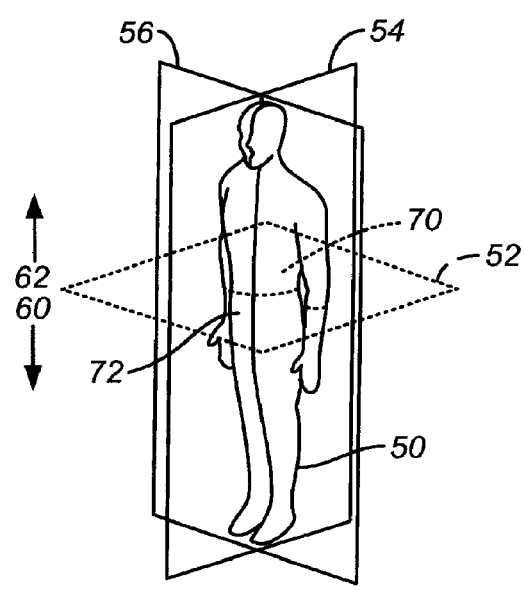
FIG. 1B is a perspective view of the anatomical planes of the human body.

In order to understand the configurability, adaptability, and operational aspects of the invention, it is helpful to understand the anatomical references of the body 50 with respect to which the position and operation of the devices and components thereof, are described. There are three anatomical planes generally used in anatomy to describe the human body and structure within the human body; the axial plane 52, the sagittal plane 54 and the coronal plane 56 (see FIG. 1B). Additionally, devices and the operation of devices are better understood with respect to the caudal 60 direction and/or the cephalad direction 62. Devices positioned within the body can be positioned dorsally 70 (or posteriorly) such that the placement or operation of the device is toward the back or rear of the body. Alternatively, devices can be positioned ventrally 72 (or anteriorly) such that the placement or operation of the device is toward the front of the body. Various embodiments of the spinal devices and systems of the present invention may be configurable and variable with respect to a single anatomical plane or with respect to two or more anatomical planes. For example, a component may be described as lying within and having adaptability or operability in relation to a single plane. For example, a stem may be positioned in a desired location relative to an axial plane and may be moveable between a number of adaptable positions or within a range of positions. Similarly, the various components can incorporate differing sizes and/or shapes in order to accommodate differing patient sizes and/or anticipated loads. The device may be used in any individual for whom use of the device is suitable, including any animal belonging to the mammalia class, such as warm-blooded, vertebrate animals.

I. DEVICES

Figure 2A:
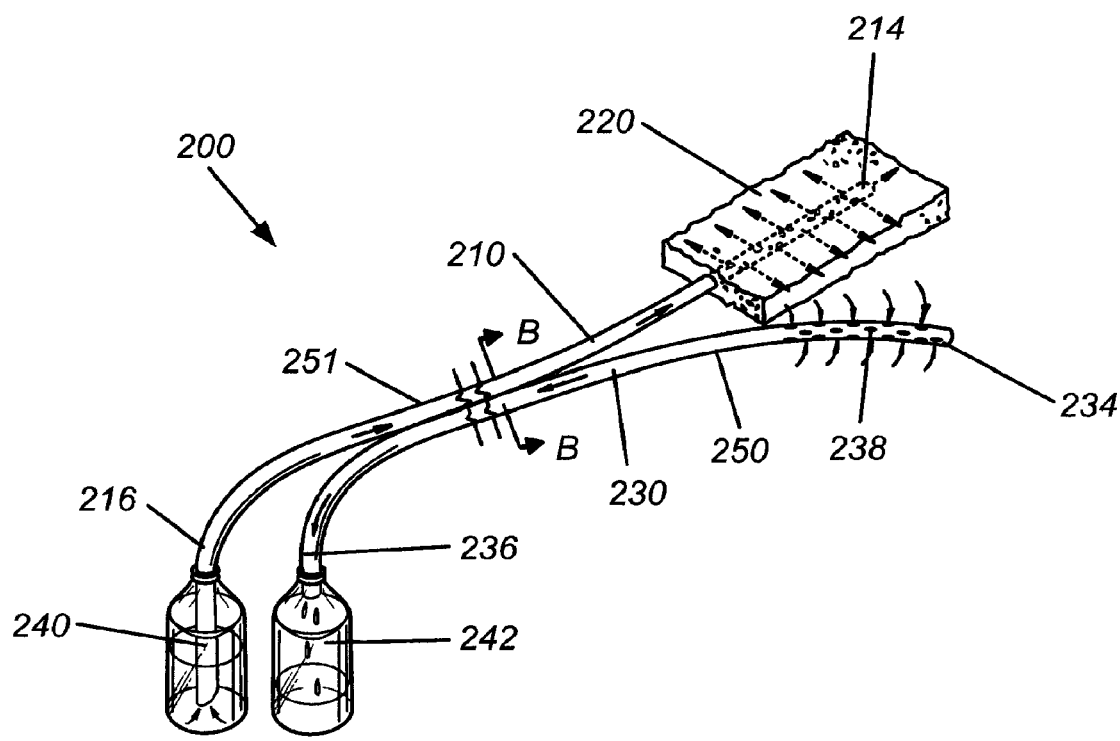
FIGS. 2A-2G illustrate a fluid delivery device and various components comprising the fluid delivery device, including an elongate body, a delivery member, and a withdrawal member.
Figure 2B:
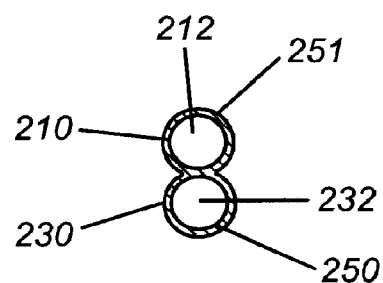

The invention described herein can be used to administer fluids to an anatomical region of the patient. FIG. 2A is a perspective view of a fluid delivery device 200. The device 200 consists of an elongate body 210, such as the tubular body illustrated, a delivery member 220, and a withdrawal member 230. The delivery member 220 facilitates delivery of a substance, e.g., inflow of a fluid, while the withdrawal member 230 facilitates removal of a substance. The walls 251 of the body 210 define the lumen 212 of the body 210 as shown in FIG. 2B. The lumen 212 can extend through the entire length of the elongate body, or it can extend through a portion of the elongate body. The lumen 212 of the body 210 is better illustrated in FIG. 2B, which shows a cross-sectional view of FIG. 2A along the line B-B. As will be appreciated by those skilled in the art, other cross-sectional shapes can be employed without departing from the scope of the invention.

The elongate body can be made out of any biocompatible, inert material. The elongate body is typically a plastic tubular structure, such as a catheter. The tubular body 210 has a distal end 214 and a proximal end 216. The distal end 214 of the tubular body is positioned within the interior of the body cavity. In the body cavity, the distal end 214 of the tubular body 210 is positioned adjacent to the anatomical region to be treated such that the device 200 is in fluid communication with a target anatomical region of the patient. The tubular body or elongate tube in general can be coated with any suitable antibiotic or anti-microbial agent to prevent infection, such as those described in U.S. Pat. No. 7,119,062 to Alvis for Methods and Compositions for Improved Articular Surgery Using Collagen; U.S. Pat. No. 6,921,541 to Chasin for Formulations and Methods for Providing Prolonged Local Anesthesia; U.S. Pat. No. 7,282,214 to Willcox for Biomedical Devices with Antimicrobial Coatings; U.S. Pat. No. 6,558,686 to Raad for Antimicrobial Coated Medical Implants; U.S. Pat. No. 7,201,745 to DiMatteo for Anti-Infective Central Venous Catheter with Diffusion Barrier Layer; U.S. Pat. No. 6,534,559 to Vanderlaan for Biomedical Devices with Hydrophilic Coatings; and U.S. Pat. No. 6,514,517 to Jamiolkowski for Antimicrobial Coatings fro Medical Devices.

In some configurations, the distal end 214 of the tubular body 210 is adapted and configured to remain in fluid communication with the proximal end 216 of the device and the exterior of the body cavity of the patient. In such a configuration, the fluid delivered by the tubular body is provided from the proximal end, e.g. via a port, which a person accesses from exterior the body. Suitable fluid can, for example, be saline. Alternatively the fluid administered can be a medicament or a therapeutic drug. The fluid can be any fluid that is suitable for administering to the region proximal to the spinal cord including, but not limited to, anesthesia, anti-inflammatory medicines, analgesics, anti-catabolites, growth factors, hormones, viral or recombinant proteins, or any other suitable fluid used for therapeutic purposes or for treatment of pain. The fluid is typically a therapeutically effective amount of medicament, or is an amount of medicament effective to facilitate a desired therapeutic effect. In an alternative configuration, the distal end 214 of the tubular body is not in fluid communication with the proximal end 216 of the device.

The device is designed so that at least a portion of the device is positioned extradurally, subfascially, subcutaneously, percutaneously, or intramuscularly. In such an embodiment, the delivery member 220 and the distal portion 214 of the tubular body 210 can be positioned within the body cavity. The proximal end 216 of the tubular body 210 is typically located outside of the body cavity. The proximal end 216 of the tubular body is in fluid communication with a fluid reservoir 240. The fluid reservoir 240 supplies the tubular body 210 with the fluid to be delivered by the delivery member 220. The fluid reservoir 240 can contain the full amount of fluid to be administered. Alternatively, the fluid reservoir can be replaced with a second fluid reservoir to deliver additionally desired amounts of fluid. In a case where the first fluid reservoir is replaced with a second fluid reservoir, the first fluid reservoir can be replaced with a second fluid reservoir containing the same fluid administered from the first fluid reservoir or containing a different fluid than the fluid administered from the first reservoir.

Figure 2C:
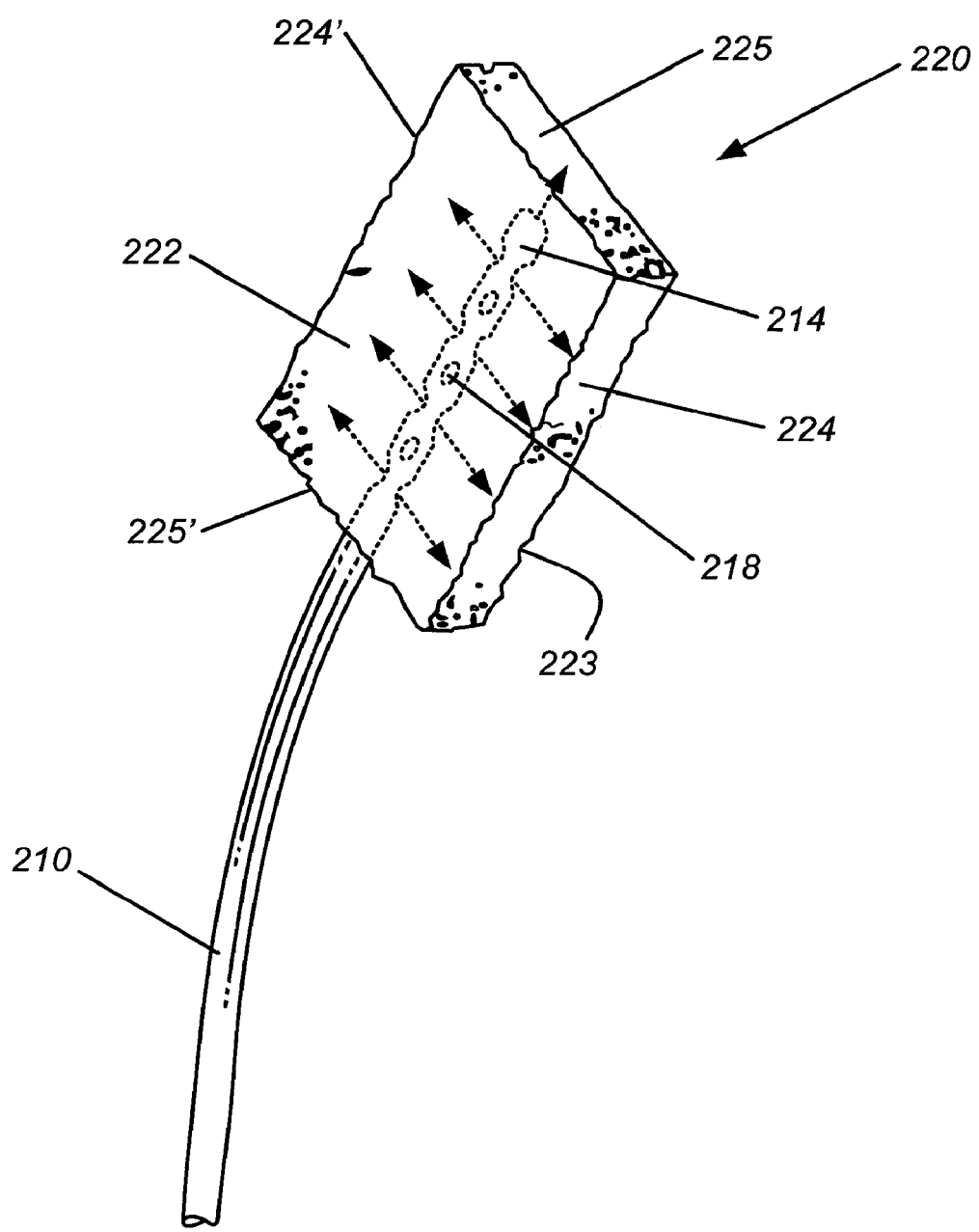

Typically, the distal end 214 of the elongate tubular body 210, as shown in FIG. 2C, is in communication with the delivery member 220. However, the delivery member can cover the entire portion of the tubular body located in the body cavity. The tubular body 210 can have one or more fenestrations 218, apertures, or perforations that facilitate the flow of fluid from the tube body 210 to the delivery member 220. In the alternative, the entire distal end 214 of the tubular body 210 can configured such that it is permeable to fluid to facilitate the transfer of fluid to the delivery member 220. For example, the distal end of the tubular body can be made of a mesh-like material or porous micro-mesh.

A delivery member 220 is shown in FIG. 2C. The delivery member 220 is typically a substantially planar delivery member, as shown in the figure. The delivery member can be in any suitable non-tubular configuration. The delivery member 220 can be sized so that it conforms to the anatomical region being treated. For example, the delivery member can be initially planar, but can be molded by the user prior to insertion so that it mimics the contours of the area to be treated. Alternatively, the delivery member can be planar when inserted but can then conform to the contours of the anatomical region after being positioned in the anatomical region. For example, the delivery member can be conformable to the curvature of the spinal cord and spinal column. The planar delivery member is typically a three dimensional structure, having a length, width, and depth where the length and width are typically greater than the depth, thus allowing the delivery member to be positioned substantially within a plane upon delivery. The fluid, after passing from the tubular body 210 to the delivery member 220, is collected in the delivery member 220. The delivery member 220 becomes saturated with the fluid in this manner. The fluid is then slowly released from the delivery member. The delivery member 220 can be configured to enable biased delivery of the fluid away from the target tissue, as opposed to delivering the fluid directly onto the target tissue.

The delivery member shown in FIG. 2C is a planar delivery member having a first exterior side 222 and second exterior side 223. After the delivery member 220 is saturated with fluid, the fluid can slowly leach out of the delivery member 220 from the first 222 or second 223 exterior sides. Additionally, fluid can leach out of the areas between the first and second sides 224,224', 225, 225'. Fluid can leach out of all surfaces simultaneously. Alternatively, fluid can leach out from a portion of the exterior. For example, the fluid can leach out of the first exterior side 222 of the delivery member, where the first exterior side is directly adjacent to the anatomically region, while not leaching out of the second exterior side 223. The delivery member can also be constructed so that fluid leaches out of any of the surfaces adjacent to the anatomical region. For example, if the first exterior side 222 is adjacent to the anatomical region, fluid can leach out of the first exterior side 222, and the areas between the first and second exterior sides, 224, 224', 225, 225', but not leach out of the second exterior side 223. Although the delivery member 220 is typically substantially planar, the delivery member 220 is not limited to this configuration. The delivery member can be any configuration suitable for the delivery of fluid including, but not limited, planar, spherical, or cylindrical configurations. Fluid can be delivered to the anatomical region using gravity wherein gravity controls the outflow of fluid from the device into the anatomical region. Gravity can also be used to drain fluid from the anatomical region. In some embodiments, the direction of fluid flow is controllable independent of gravity, for example, through the use of a pump mechanism. Typically, the device is configured such that the rate and volume of fluid delivery at the tissue site is controlled by the delivery member.

In one aspect, the delivery member can have predefined passages for passing fluid to the bodily area to be treated. In another aspect, the delivery member is a porous delivery member. The delivery member can be made of a bioresorbable material or matrix or a bioresorbable sponge. The bioresorbable matrix in some embodiments is a matrix made of a biocompatible material that envelopes another agent to be administered in the matrix. As the bioresorbable matrix is resorbed, the additional agent can be released to the anatomical regions. Any suitable agent can be incorporated with the bioresorbable matrix including, but not limited to, proteins. The delivery member can be selected from at least one of the following: a biocompatible matrix, a polymer, a collagenous sponge, or a resorbable biocompatible mater, such as a hydrogel. The delivery member can be made out of a synthetic polymeric material. Alternatively, the delivery member can be made out of a natural polymeric material. The delivery device can further be made of a biodegradable material.

The porosity, or density, of the delivery member facilitates the constraining of the fluid in the delivery member, the releasing of the fluid from the delivery member in a controlled manner, and substantially preventing the spreading of the fluid outside the area of intended treatment. Therefore, one way of controlling the rate and volume of fluid administered is through the delivery member. The delivery member allows the anatomical area to absorb the fluid being released at a rate consistent with the slow release from the delivery member, while preventing the fluid from contacting, for example, nerves in proximity to the bodily area, since only small amounts of fluid are contacting the area at any one time. In other words, before the fluid reaches the nerves, the fluid is absorbed by the surrounding anatomy. In a case where the device is used post-operatively to treat pain associated with spinal surgery, or surgery in general, diffusion and extravasation of the medicament to the surrounding anatomical region is substantially limited by the porous delivery member. The rate of delivery can be controlled by using delivery members that range in their sizes and densities, or which have layers of materials having different rates of resorption and/or which are configured to deliver different substances.

The delivery rate of the device can further be controlled externally through the use of a sensor located on the delivery member in communication with the delivery reservoir and a controller. The controller is adapted to control the rate at which the fluid is delivered by the delivery member based on information received from the sensor. The sensor can be adapted to determine one or more parameters from the patient at the delivery site including, for example, the concentration of the fluid, the rate of flow, or any other measurable parameter that would be suitable. In such an embodiment, the concentration of the fluid is set to a desired level and is monitored. If the concentration detected increases above or decreases below this level, the rate of flow of the fluid can be adjusted. Alternatively, the flow rate of the fluid delivered to the patient is another parameter that may be detected and monitored. The sensor can monitor the amount of fluid entering into, and optionally leaving, the anatomical region and adjust the rate of flow accordingly. Any suitable parameter that may be monitored may be used. Also, multiple sensors may be used to measure more than one parameter simultaneously.

Figure 2D:
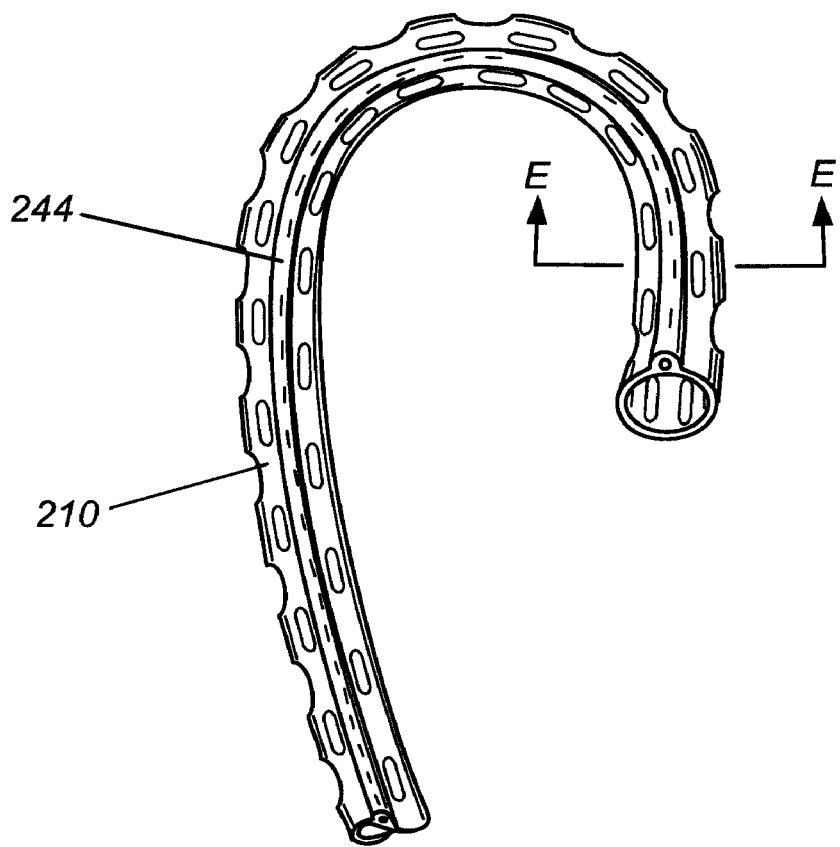
Figure 2E:
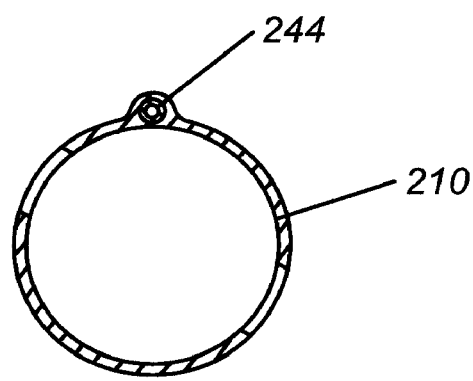

The device provided herein, in some embodiments, is a steerable device. In other words, the device is capable of being manipulated by the user, such that the user can orient the device as desired. One way the device can be manipulated is by further incorporating a structure adapted to steer the device. Typically, the device further comprises a malleable wire 244 located within the tubular body 210 of the device, as shown in FIG. 2D. FIG. 2D shows a portion of the tubular body 210 incorporating a wire 244 along part of the length of the tubular body 210. The wire 244 can be incorporated along the entire length of the tubular body. Alternatively, the wire can be incorporated along only the distal end of the tubular body. FIG. 2E is a cross-section of FIG. 2D along line E-E. The wire can be located on one side of the tubular body 210 as shown in FIG. 2E. Alternatively, more than one wire can be used. Multiple wires can be used and positioned at multiple positions along the tubular body. The tubular body can also be constructed so that the entire tubular body is constructed from a frame of malleable wires covered with the inert material of the tubular body.

The device for delivering fluid typically comprises a withdrawal element as shown in FIG. 2A. The withdrawal member is 230 typically used to remove extra fluid located in the anatomical region where the device is being used. At least a portion of the withdrawal member 230 is adapted to be at least partially positioned extradurally, subfascially, subcutaneously, percutaneously, or intramuscularly. The distal end 234 of the withdrawal member is positioned so that it is in close proximity to the delivery member and distal end 214 of the tubular body 210. The distal end 234 of the withdrawal member typically consists of fenestrations 238 or perforations into which the fluid to be removed from the anatomical region flows. Alternatively, the distal end of the withdrawal element can also be made of any suitable porous or mesh-like material. The walls 250 of the withdrawal member 230 define the lumen 232 of the withdrawal member 230 as shown in FIG. 2B. The lumen can extend through the entire length of the withdrawal member or can extend through a portion of the withdrawal member. The withdrawal member can also be coated with anti-microbial or antibiotic agents, as described above.

The proximal end 236 of the withdrawal element 230 is typically located outside of the body cavity and is in fluid communication with a disposal reservoir 242. The disposal reservoir 242 can be permanently attached to the withdrawal element 230 for one time use. Alternatively the disposal reservoir 242 can be detachable to facilitate emptying and reuse. After emptying the disposal reservoir 242 can be reattached. In some embodiments a vacuum or any other suitable device for applying reduced pressure can be used with the withdrawal member to facilitate the removal of fluid from the anatomical region. The suction created by the vacuum can be used to further control the rate at which the fluid from the delivery member is leached into the anatomical region, by increasing or decreasing the negative pressure in the anatomical region. A combined delivery/drainage safety mechanism can also be incorporated into the device to control the rate of fluid delivery as compared to the rate of fluid removal.

Figure 2F:
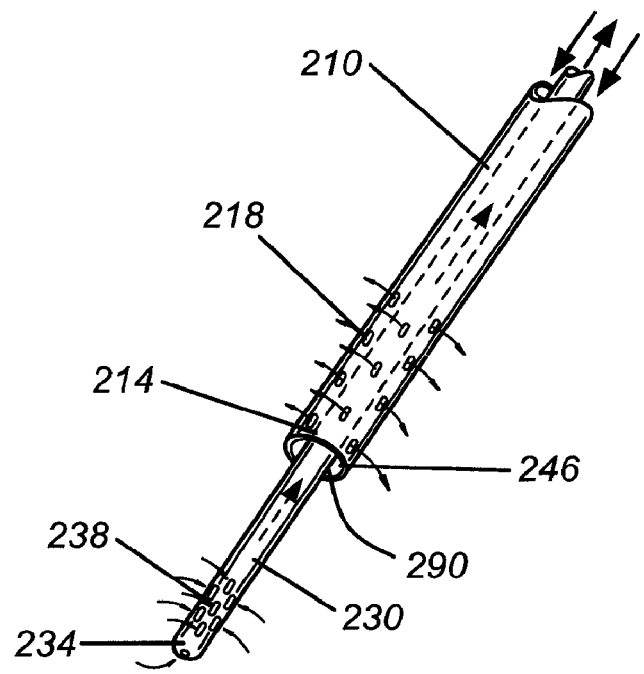

Alternative embodiments of the device can be used. For example, the withdrawal member and the tubular body can be nested along at least a portion of their lengths. In one embodiment, tubular body 210 houses the withdrawal element 230 as shown in FIG. 2F. The withdrawal element 230 is inserted within the tubular body 210, and in some cases is positioned so that the distal end 234 of the withdrawal element 230 extends past the distal end 214 of the tubular body 210. The distance which the distal end 234 of the withdrawal member 230 extends past the distal end 214 of the tubular body 210 can be adjustable and can further be defined by the user. The distal end 214 of the tubular body 210 has fenestrations 218 from which fluid passes into the anatomical region. Additionally, the withdrawal element 230 interfaces with the tubular body 210 through a seal 290 which blocks the end 246 of the tubular body 210 so that fluid only passes out of the tubular body 210 through the fenestrations 218. Similarly, the distal most portion of the distal end 234 of the withdrawal element 230 has fenestrations 238 into which fluid is drained into the withdrawal element 230. The remainder of the withdrawal element 230, or the portion of the withdrawal element housed within the tubular body 210, is solid and impermeable to fluids. Thus, the fluid in the lumen of the withdrawal member is isolated from the fluid in the lumen of the tubular body.

Figure 2G:
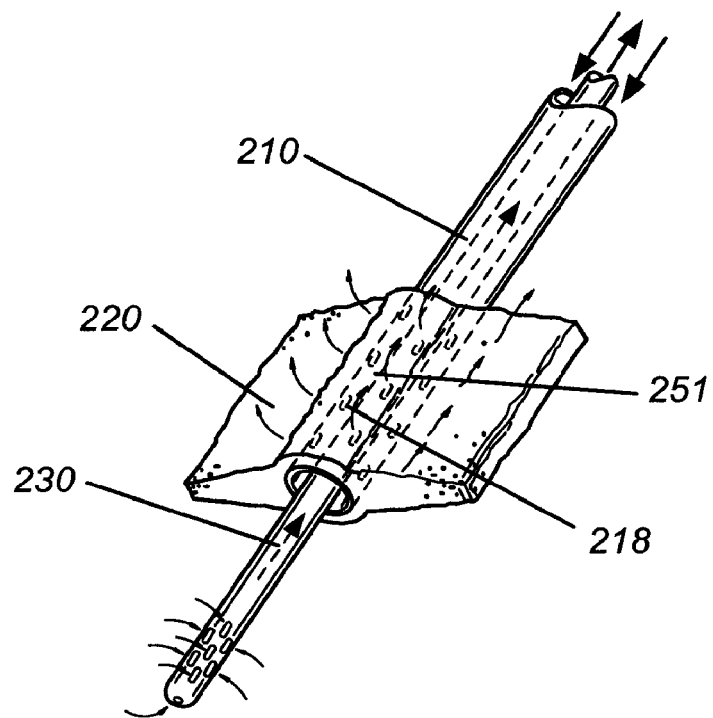

The nested withdrawal member 230 and tubular body 210 can further consist of a delivery member 220, as shown in FIG. 2G. The delivery member 220 is placed over the tubular body 210, specifically over the fenestrations 218 located on the tubular body 210. The delivery member 220 is therefore in fluid communication with the lumen 212 of the tubular body 210 through the fenestrations 218 in the wall 251 of the tubular body 210. In some embodiments, the delivery member 220 is disposable. In such an embodiment, the delivery member 220 can be detached from the tubular body 210 and a new delivery member attached to the tubular body 210. In a further embodiment of the device, the elongate body and delivery member are introducible into the body cavity in the proximity of the anatomical region. Once the delivery member has been positioned in the desired location, the elongate body infuses the delivery member with fluid. The elongate member can then be detached from the delivery member and withdrawn from the body cavity leaving only the delivery member in position inside the body cavity. The delivery member then releases fluid slowly over time. In such an embodiment, the delivery member is typically a biodegradable or bioresorbable matrix that will be resorbed by the body over time. Any suitable embodiment of the delivery member previously described can be used.

Figure 3A:
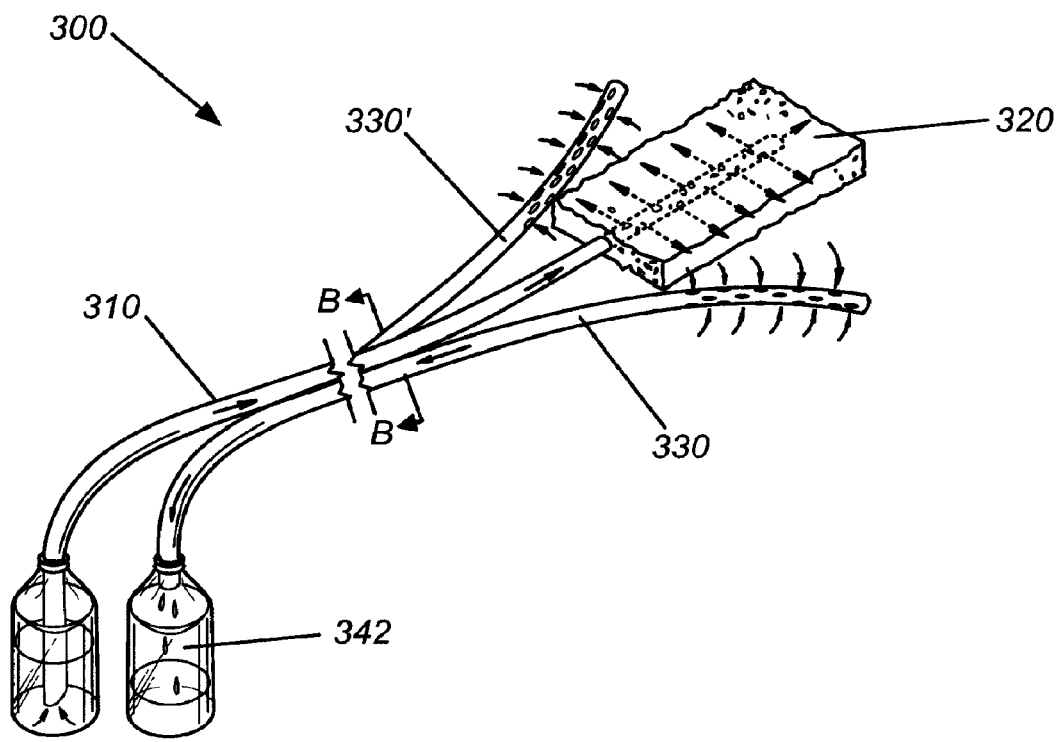
FIG. 3A illustrates a fluid delivery device comprising multiple withdrawal members.
Figure 3B:
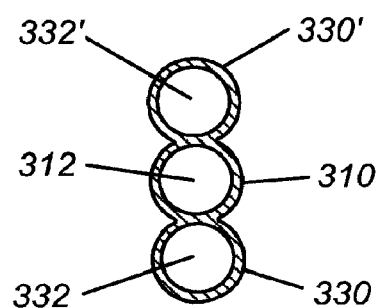
FIG. 3B is a cross section of the delivery device of FIG. 3A.

Typically, the device consists of one withdrawal member with one distal end as shown in FIG. 2A. In some embodiments, however, more than one withdrawal member can be used in the device 300 as shown in FIG. 3A. In embodiments where more than one withdrawal member is used, the withdrawal members 330, 330' can be located on opposite sides of the tubular body 310 and the delivery member 320, as shown in the FIG. 3A. A cross section of the tubular body 310 and withdrawal members 330, 330' along line B-B and the respective lumens, 312, 332, 332', is shown in FIG. 3B. Alternatively, the withdrawal members can be located on the same side of the tubular body and the delivery member. FIG. 3A shows more than one withdrawal member, both of which drain into one disposal reservoir 342. Alternatively, each withdrawal member can drain into its own disposal reservoir. The withdrawal member is typically coated with an antibiotic or anti-microbial agent to prevent infection and can be coated with any suitable antimicrobial or antibiotic.

Figure 4:
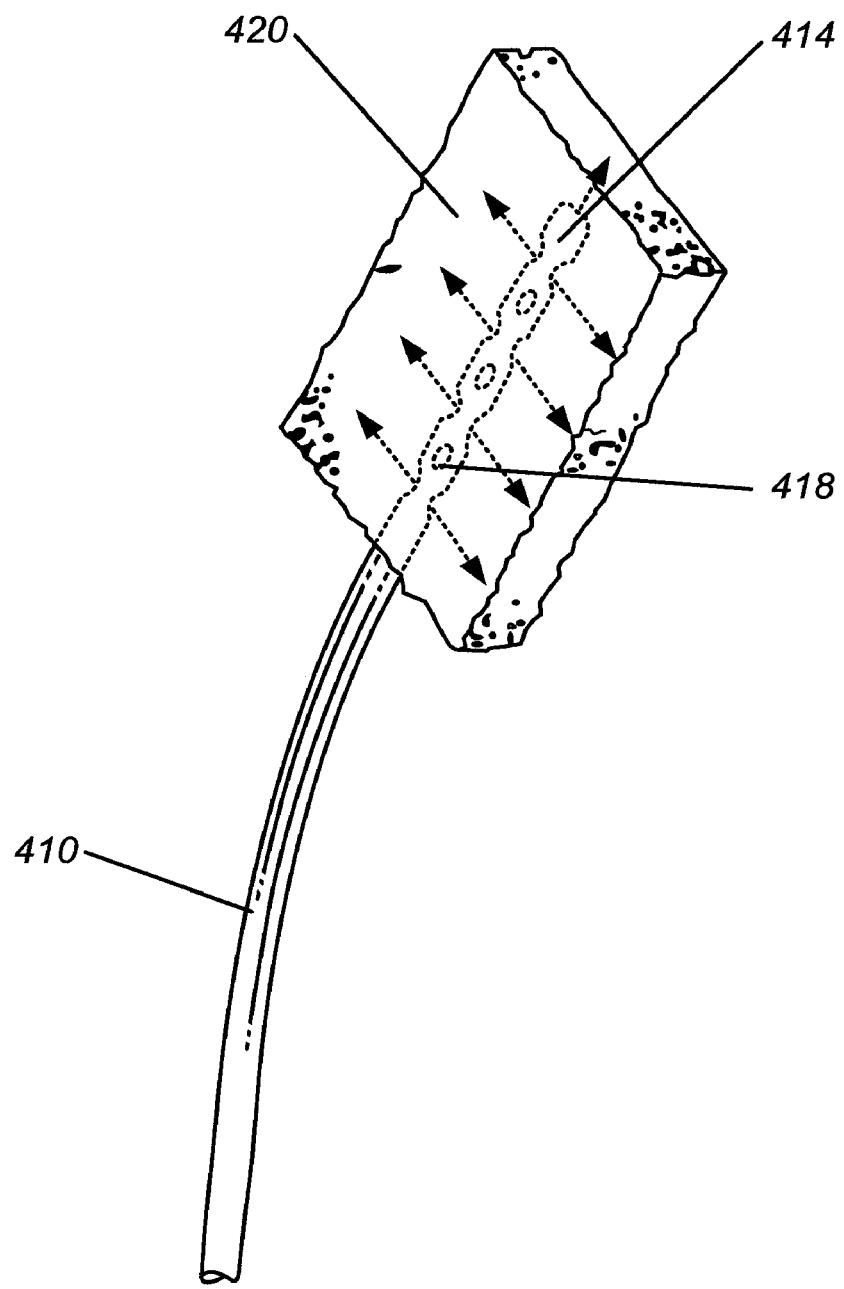
FIG. 4 is an illustration of a fluid delivery device comprising an elongate body and a delivery member, and not comprising a withdrawal member.

Although the device typically used comprises an elongate body and a delivery member together with a withdrawal member, it will be appreciated that the device may comprise only a tubular body 410 together with a delivery member 420, and does not comprise a withdrawal member, as shown in FIG. 4. In such an embodiment, the delivery member 420 is in fluid communication with the tubular body 410 through fenestrations 418 or perforations located on the distal end 414 of the tubular body 410. The proximal end of the tubular body is in fluid communication with a fluid reservoir. Any of the previously mentioned embodiments of the tubular body 410 and the delivery member 420 can be used with this embodiment. The delivery member 420 can be configured to enable biased delivery of the fluid away from the target tissue, as opposed to delivering the fluid directly onto the target tissue.

Figure 5A:
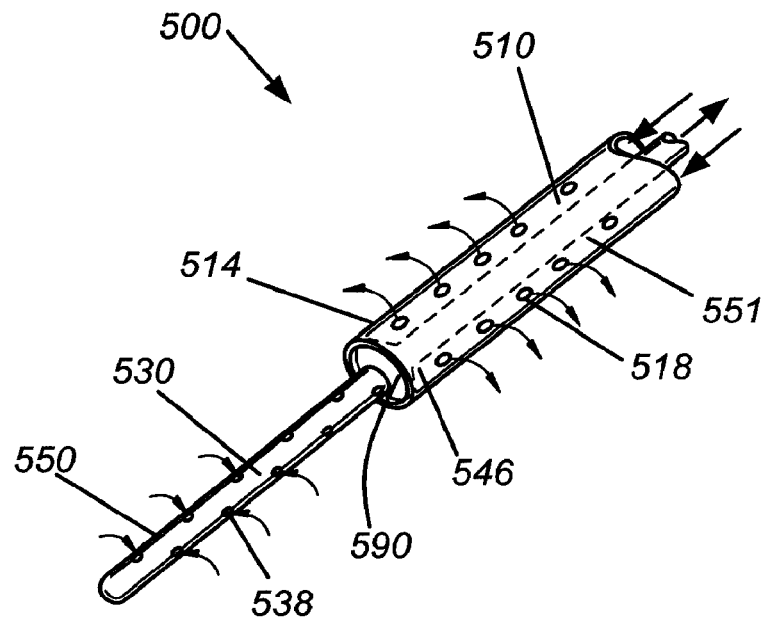
FIGS. 5A-5C illustrate a fluid delivery device with a withdrawal element nested within the elongate body and where the withdrawal element is fixed with respect to the elongate body and a cross-section thereof.
Figure 5B:
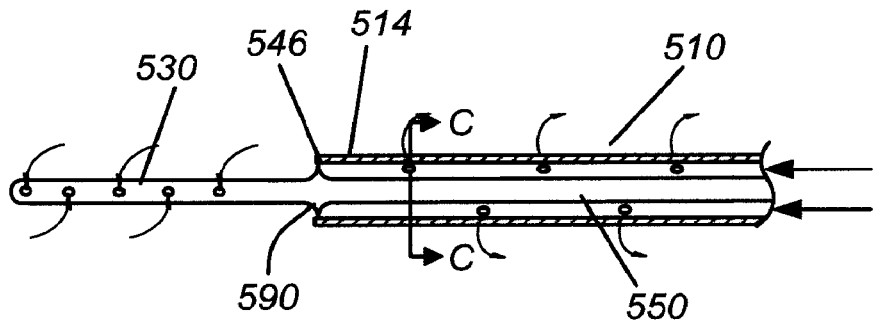
Figure 5C:
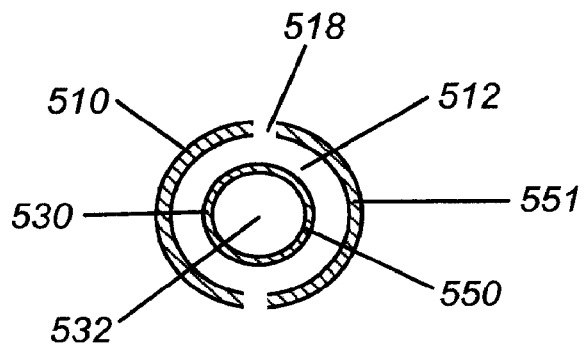

Alternative embodiments of a fluid delivery device 500 in which a portion of the withdrawal member 530 is nested within the tubular body 510 can be anticipated. FIG. 5A shows a delivery device 500 where the withdrawal member 530 is nested within the tubular body 510, and where the withdrawal member 530 is extended past the end of the distal end 514 of the tubular body 510. FIG. 5A further shows a withdrawal element 530 that has been fixed in position relative to the tubular body 510. In such embodiment the end 546 of the distal end 514 of the tubular body 510 is bonded with the withdrawal member 530, to create a barrier 590 that prevents the outflow of fluid from the end 546 of the distal end 514 of the tubular body 510. The fluid that flows out of the tubular body 510 thus does so only through the fenestrations 518 in the wall 551 of the tubular body 510. Similarly, fluid flows into the withdrawal member 530 through fenestrations 538 located in the wall 550 of the withdrawal member 530. FIG. 5B is a lateral cross-section through the device where the tubular member 510 is bonded to the withdrawal member 530. FIG. 5B further shows how an internal wall 550 in the tubular body 510 separates the fluid to be delivered to the anatomical region from the fluid drained from the anatomical region. FIG. 5C is a cross-section of the device 500 shown in FIG. 5B along the line C-C. As shown in FIG. 5C, the lumen 532 of the withdrawal element 530 is isolated from the lumen 512 of the tubular body by a solid internal wall 550 forming the lumen 532 of the withdrawal element 530. Fluid located in the lumen 532 of the withdrawal element 530 is therefore isolated from the fluid within the lumen 512 of the tubular element 510. Fluid exits from the lumen 512 of the tubular body 510 through the fenestrations 518 located in the wall 551 of the tubular body 510. In some embodiment, a delivery member is in fluid communication with the distal end of the tubular body.

Figure 6A:
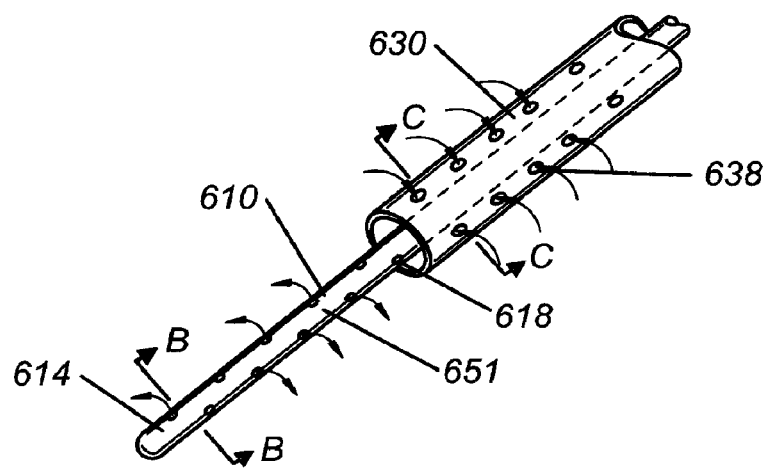
FIGS. 6A-6C illustrates a fluid delivery device in which the elongate body is nested within the withdrawal element and a cross-sections thereof.
Figure 6B:
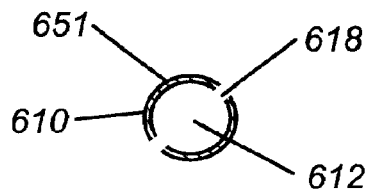
Figure 6C:
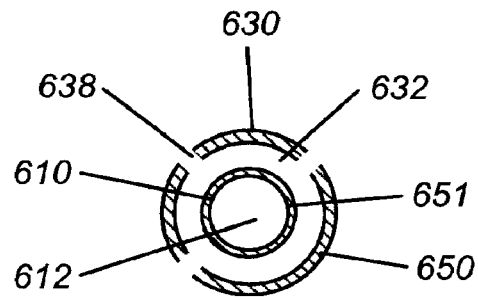

An alternate embodiment of the device described herein consists of a tubular body 610 nested within a withdrawal member 630 as shown in FIG. 6A. In such an embodiment, the distal end 614 of the tubular body 610 can be extended past the distal end 634 of the withdrawal member 634. Fenestrations 618 in the wall 651 of the tubular body 610 allow the fluid to exit from the lumen 612 of the tubular body 612. A cross section of the tubular body 610 along line B-B in FIG. 6A is shown in FIG. 6B. The cross-section of the tubular body 610 shows how fenestrations 618 in the wall 651 of the tubular body 610 permit fluid to exit the lumen 612 of the tubular body 610. FIG. 6C is a cross-section of FIG. 6A along the line C-C. As seen in FIG. 6C, the fluid in the lumen 612 of the tubular body 610 is isolated from the fluid in the lumen 632 of the withdrawal member 630 by an internal wall 651. The wall 651 that defines the lumen 612 of the tubular body 610 is solid for the entire length of the tubular body 610 housed within the withdrawal member 630. Fenestrations 638 in the wall 650 of the withdrawal member 630 provides a mechanism for fluid to enter the lumen 632 of the withdrawal member 630. In some embodiments, a delivery member is in fluid communication with the distal end of the tubular body.

Figure 7A:
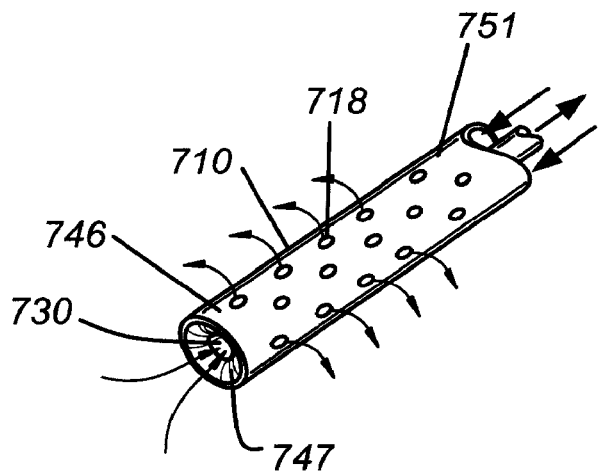
FIGS. 7A-7C illustrates a fluid delivery device with a withdrawal member nested in the elongate body.
Figure 7B:
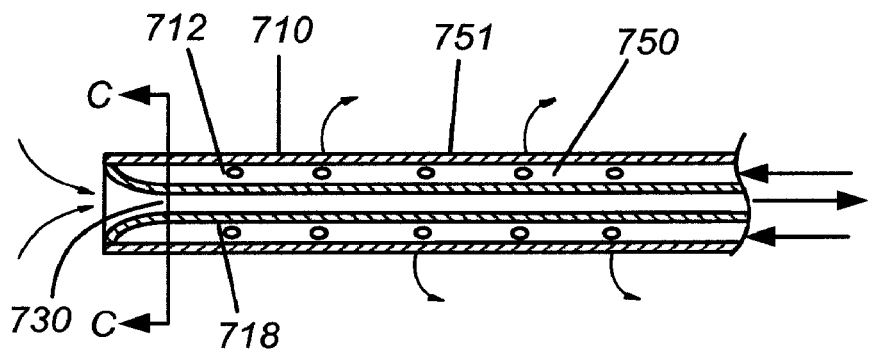
Figure 7C:
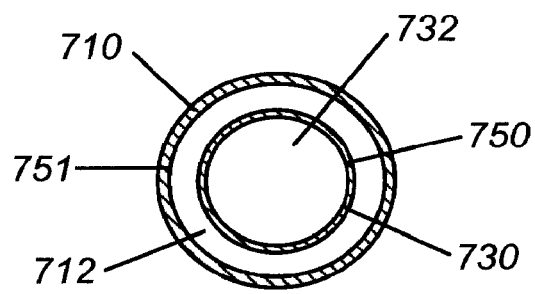

In some embodiments where the withdrawal member 730 is nested within the tubular body 710, the end 747 of the withdrawal member 730 is flush with the end 746 of the tubular body 710. Such an embodiment is shown in FIG. 7A. FIG. 7A is a perspective view of the device 700 in which the end 747 of the withdrawal member 730 is flush with the end 746 of the tubular body 710, and does not extend past the end 746 of the tubular body 710. Fenestrations 718 in the wall 751 of the tubular body 710 allow fluid to flow out of the tubular body 710. FIG. 7B is a lateral cross-section of the device 700 shown in FIG. 7A. In FIG. 7B, the wall 750 of the withdrawal member 730 is impermeable to fluid transfer. The wall 751 of the tubular body 710 has fenestrations 718 that permit fluid to flow out of the lumen 712 of the tubular body 710 into the anatomical region. FIG. 7C is a cross-section of the device shown in FIG. 7B along line C-C. FIG. 7C illustrates how the wall 750 of the withdrawal member 730 is impermeable to fluid, thus preventing the fluid in the lumen 732 of the withdrawal member 730 from mixing with the fluid in the lumen 712 of tubular body 710. FIG. 7C also illustrates a cross-section of the device where no fenestrations are present in the wall 751 of the tubular member 710. In such a region of the tubular body no fluid exits the lumen of the tubular body. In some embodiments, a delivery member is in fluid communication with the distal end of the tubular body.

Figure 8A:
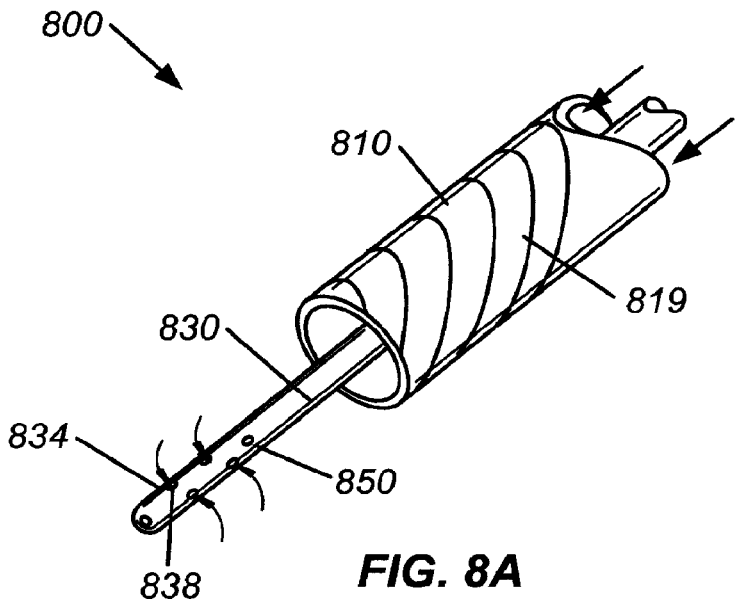
FIGS. 8A-8C illustrates a fluid delivery device with a spiral cut elongate body.
Figure 8B:
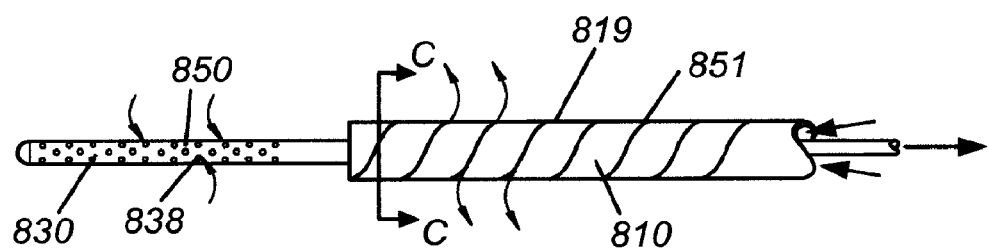
Figure 8C:
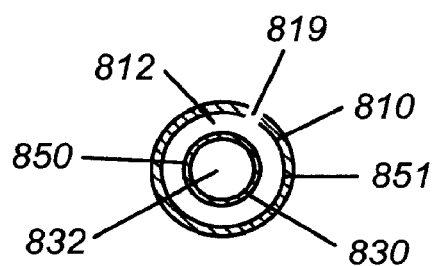

In another aspect of the device described herein, the device 800 comprises a spiral cut tubular body 810, as shown in FIG. 8A. In such an embodiment, the withdrawal member 830 is nested within the spiral cut tubular body 810. The distal end 834 of the withdrawal element 830 has fenestrations 838 in its wall 850 which permits fluid from the anatomical region to flow into the withdrawal element 830. The tubular body 810 in such an embodiment is spiral cut and permits fluid to flow out of the tubular body 810 through the spiral cuts 819. A lateral view of the device is shown in FIG. 8B. A cross-section of the device 800 shown in FIG. 8B, along line C-C is shown in FIG. 8C. The cross sectional view illustrates how the wall 850 of the withdrawal element 830 is impermeable to fluid transfer between the lumen 832 of the withdrawal member 830 and the lumen 812 of the tubular body 810. The spiral cut 819 in the wall 851 creates a passageway for fluid in the lumen 812 of the tubular body 810 to pass into the anatomical region. In some embodiments, a delivery member is in fluid communication with the distal end of the tubular body.

Figure 9A:
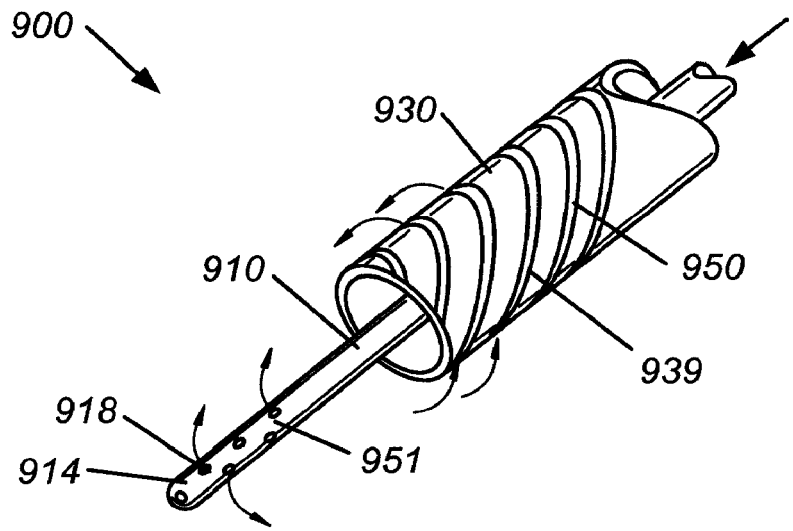
FIGS. 9A-9C illustrates a fluid delivery device with a spiral cut withdrawal element.
Figure 9B:
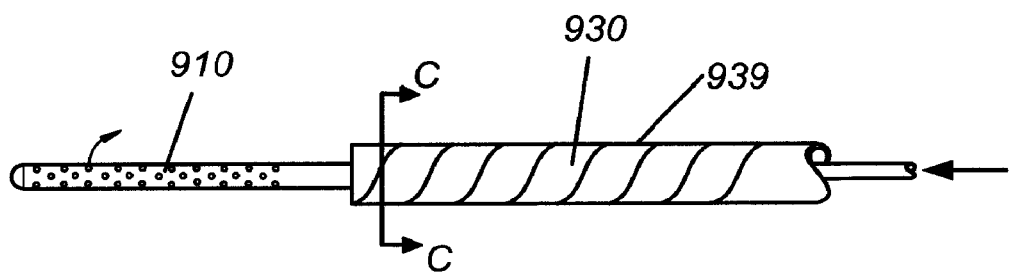
Figure 9C:
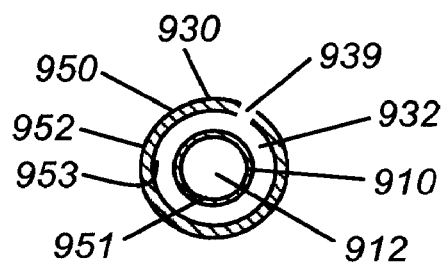

The spiral cut principle can be used in devices where the tubular body is nested in the withdrawal member. In such an embodiment, the withdrawal member 930 has spiral grooves traversing around the withdrawal member 930, as shown in FIG. 9A. Fenestrations 918 in the wall 951 of the tubular body 910 permits fluid to exit out of the tubular body 910. Instead of fenestrations in the wall 950 of the withdrawal member 930, a spiral groove 939 circles around the withdrawal member 930. The groove 939 in the withdrawal member 930 serves to draw fluid into the groove 939 and along the length of the withdrawal member 930 away from the distal end of the device 914. In some cases, both fenestrations and a groove may be present in the wall of the withdrawal member. FIG. 9B is a lateral view of the device 900 with a withdrawal member 930 having a spiral groove 939. FIG. 9C is a cross section of the device shown in FIG. 9B along line C-C. As is seen in FIG. 9C, the wall 951 of the tubular body 910 is impermeable to fluid, thus preventing the mixing of fluid between the fluid located in the lumen 932 of the withdrawal member 930 with the fluid located in the lumen 912 of the tubular member 910. Further shown in FIG. 9C is an embodiment where only a groove 939 is located in the wall 950 of the withdrawal member 930. The groove 939 runs through the exterior surface 952 of the wall 951 but does not pass through the interior surface 953 of the wall. The lumen 932 of the withdrawal member 930 remains fluid-less. In an embodiment where both fenestrations and a groove are present in the wall of the withdrawal member, fluid can flow into the lumen of the withdrawal member and can be carried away along the groove in the wall of the withdrawal member. In some embodiment, a delivery member is in fluid communication with the distal end of the tubular body.

Figure 10A:
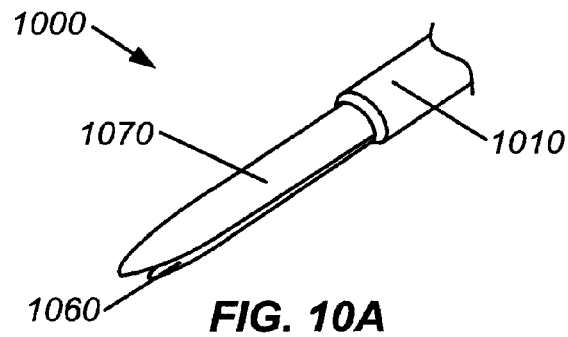
FIGS. 10A-10F illustrates a fluid delivery device with a retractable stylus and a fiberous channel for delivering fluid.
Figure 10B:
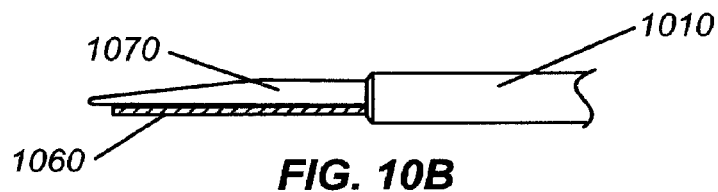
Figure 10C:
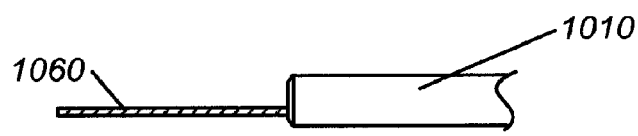
Figure 10D:
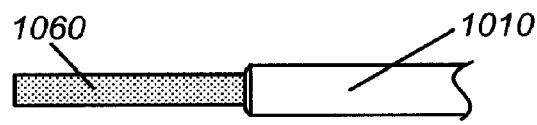
Figure 10E:
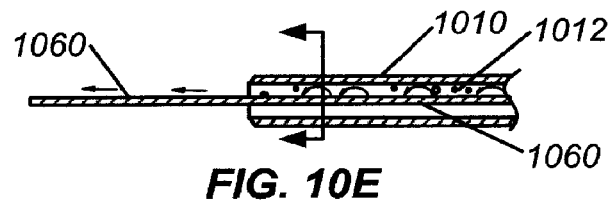
Figure 10F:
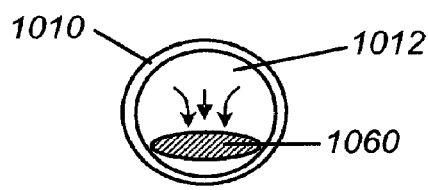

The device described herein can further consist of a tubular body and flattened delivery member for administering fluid to the anatomically region. The tubular body 1010 with flattened delivery member 1060 is shown in FIG. 10A. In FIG. 10A the device 1000 comprises a tubular body 1010 with a fibrous channel 1060 serving as the delivery member, and a stylus 1070. The fibrous channel 1060 can be a braided fibrous channel that serves to draw fluid down its length, e.g. by drawing fluid along its length using a capillary action, away from the elongate body and administers the fluid to the anatomical region it contacts with a controlled rate of release or delivery. The stylus 1070 aids in the positioning of the fibrous channel 1060 in the anatomical region. FIG. 10B is a side view of the stylus embodiment of the device 1000. The stylus 1070 is typically positioned above the fibrous channel 1060, as is shown in FIG. 10B. However, the stylus 1070 can be positioned in any orientation relative to the fibrous channel including but not limited to being positioned to either side of the fibrous channel, underneath the fibrous channel, or at any angle relative to the fibrous channel 1060. FIG. 10C is an illustration of the stylus embodiment of the device 1000 as viewed from the side in which the stylus shown in FIG. 10B has been retracted and leaving only the fibrous channel 1060. FIG. 10D is a top view of the device and fibrous channel 1060 in which the stylus has been retracted. FIG. 10E shows a lateral cross-section through the stylus embodiment of the device as shown in FIG. 10C. As can be seen in FIG. 10E, the lumen 1012 of the tubular body 1010 is in contact with the fibrous channel 1060. In essence, fluid saturates the fibrous channel 1060 and then slowly leaches out of the fibrous channel 1060. FIG. 10F is a cross section of the device shown in FIG. 10E along the line F-F, illustrating how the fibrous channel 1060 is located within the lumen 1012 of the tubular body 1010 and comes into contact with the fluid in the tubular body 1010.

Figure 11A:
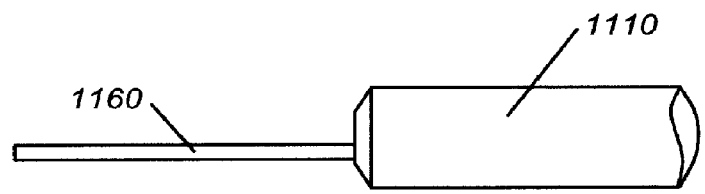
FIGS. 11A-11D illustrates a fluid delivery device with a fibrous delivery channel and a fibrous withdrawal member surrounding the delivery channel.
Figure 11B:
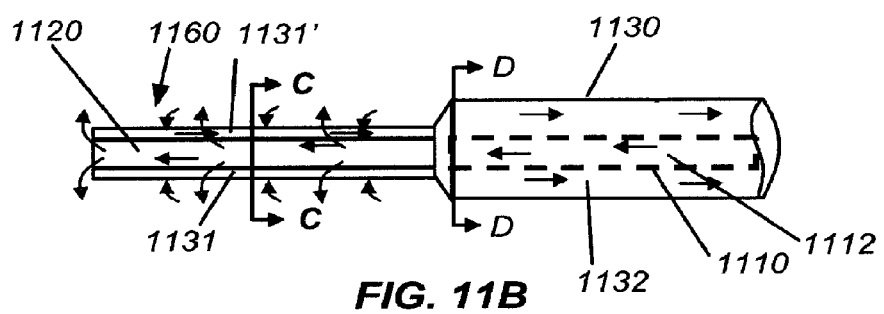
Figure 11C:
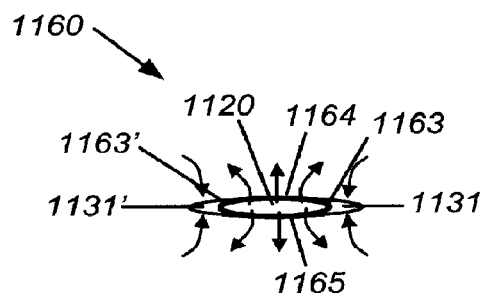
Figure 11D:
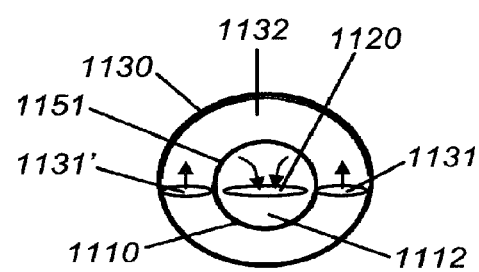

An alternate embodiment of the stylus embodiment is shown in FIG. 11A. FIG. 11A is a side view of the stylus embodiment of the device comprising a tubular body 1110 and fibrous channel 1160, and in which the stylus has already been retracted. FIG. 11B is a top view of the stylus embodiment of the device in which the stylus has been retracted showing a fibrous channel 1060 that can be used to both deliver fluid through the delivery portion 1120 of the fibrous channel 1060 and can also be used to draw fluid away from the anatomical region through the withdrawing portions 1131, 1131' of the fibrous channel 1160. The lumen 1112 of the tubular body 1110 is in fluid communication with the delivery portion 1120 of the fibrous channel 1160, whereas the lumen 1132 of the withdrawing member 1130 is in fluid communication with the withdrawing portions 1131, 1131' of the fibrous channel 1160. FIG. 11C is a cross-section of the fibrous channel 1160 along the line C-C as shown in FIG. 11B. The delivery portion 1120 is isolated from the withdrawing portion 1131, 1131', by an insulating layer 1163, 1163' located on each side of the delivery portion 1120 between the delivery portion 1120 and the withdrawing portions 1131, 1131'. Fluid is leached out of the delivery portion 1120 from the top 1164 and bottom 1165 of the delivery portion 1120. Fluid is then absorbed by the withdrawing portions 1131, 1131' of the fibrous channel 1160. FIG. 11D is a cross section of FIG. 11B along line D-D illustrating how the delivery portion 1120 of the fibrous channel is in fluid communication with the lumen 1112 of the tubular body 1110. The withdrawing portions 1131, 1131' are in fluid communication with the lumen 1132 of the withdrawing member 1130. The fluid in the lumen 1112 of the tubular body 1110 is isolated from the fluid in the lumen 1132 of the withdrawing member 1130 by the wall 1151 defusing the lumen of the tubular body 1110.

Figure 12:
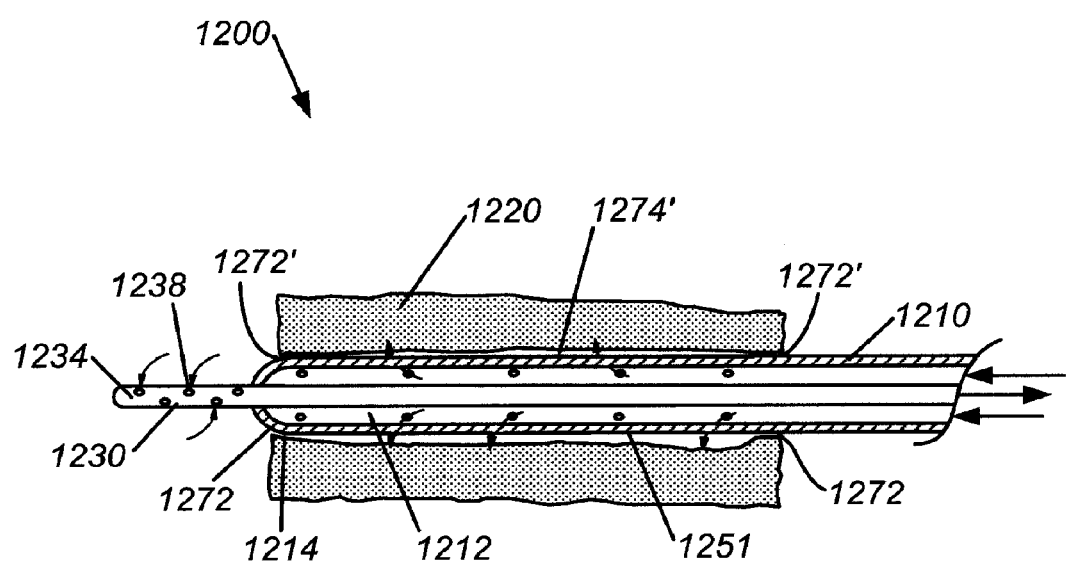
FIG. 12 is an illustration of a device with a chamber between the delivery member and the elongate body.

FIG. 12 illustrates an embodiment of the device 1200 in which the withdrawing member 1230 is nested within the tubular body 1210 as previously described, but which further comprises a delivery member 1220 bonded to the tubular body 1210 at bonding sites 1272, 1272'. The figure illustrates how the distal end 1234 of the withdrawing member 1230 extends past the distal end 1214 of the tubular body 1210. Fenestrations or perforations 1238 in the distal end 1234 of the withdrawing member 1230 permits the flow of fluid into the withdrawing member 1230. Because the delivery member 1220 is bonded to the tubular body 1210 at bonding sites 1272, 1272', a chamber 1274' is formed between the delivery member 1220 and the tubular body 1210. Fluid flowing out of the fenestrations 1212 in the wall 1251 of the tubular chamber 1210 collects first in the chamber 1274 before being absorbed by the delivery member 1220. In such an embodiment, the fluid is uniformly absorbed by the delivery member 1220 along the entire length of the delivery member.

Figure 13:
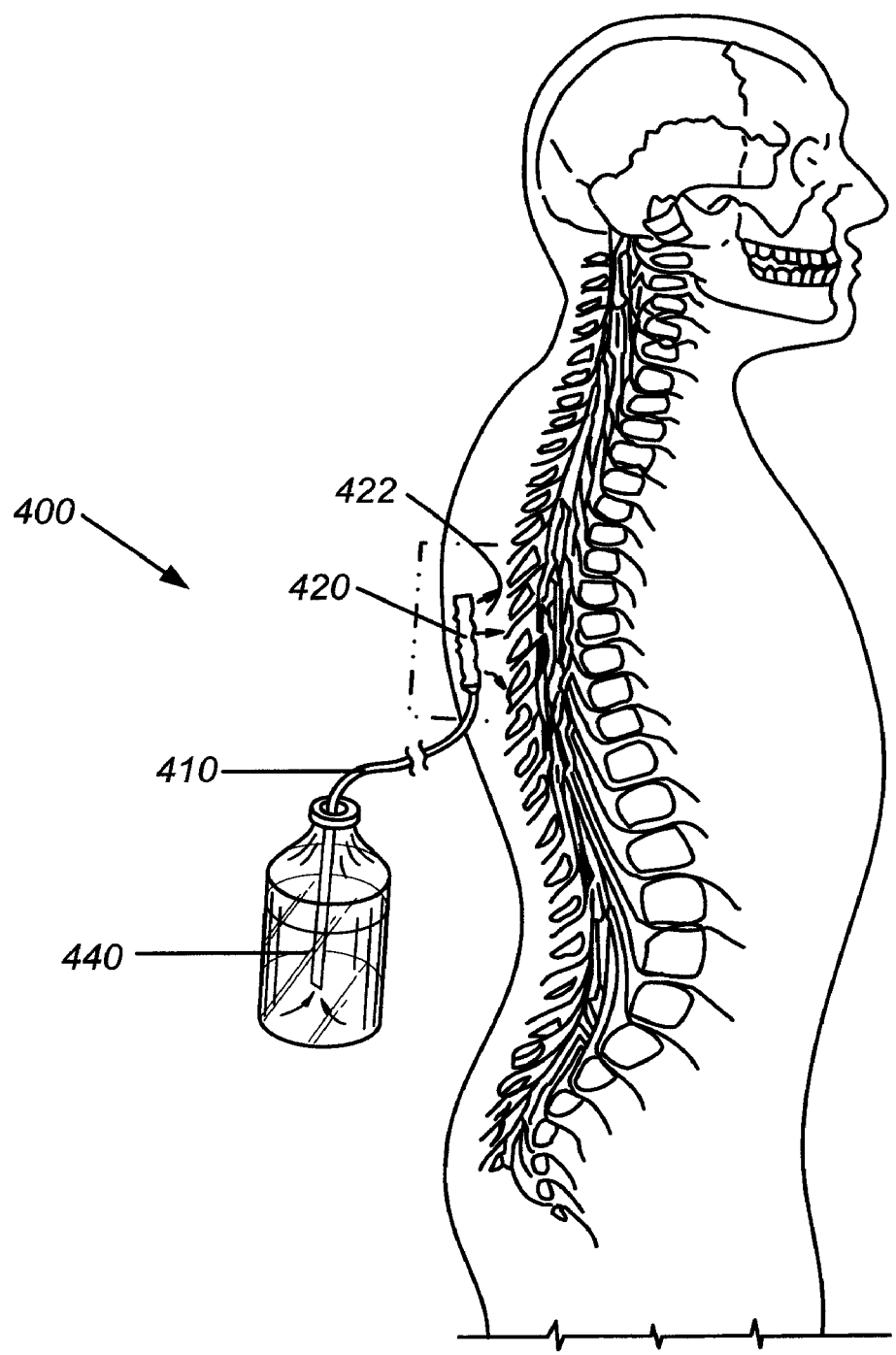
FIG. 13 illustrates a fluid delivery device in use, without a withdrawal member.

FIG. 13 illustrates a device 400 with a planar delivery member 420 in use as viewed through a sagittal plane of the body. The device 400 does not include a withdrawal member. In FIG. 13, the device is positioned dorsally such that the planar delivery member of the device is positioned to provide its largest surface area largely within a coronal plane. The positioning of the device enables it to provide treatment for pain associated with spinal surgery. The device 400 has been placed in the posterior of the patient such that the first surface 422 of the device 400 is adjacent to the anatomical region to be treated, in this case the area encompassing thoracic region of spine. Fluid from a fluid reservoir 440 is introduced to the region through the tubular body 410 and the delivery member 420. Fluid is released from the first surface 422 of the device.

Figure 14B:
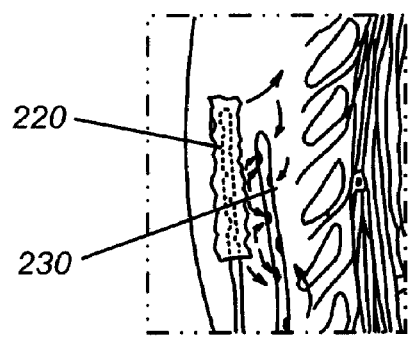
FIG. 14B is a close-up view of the fluid delivery device in use.
Figure 14A:
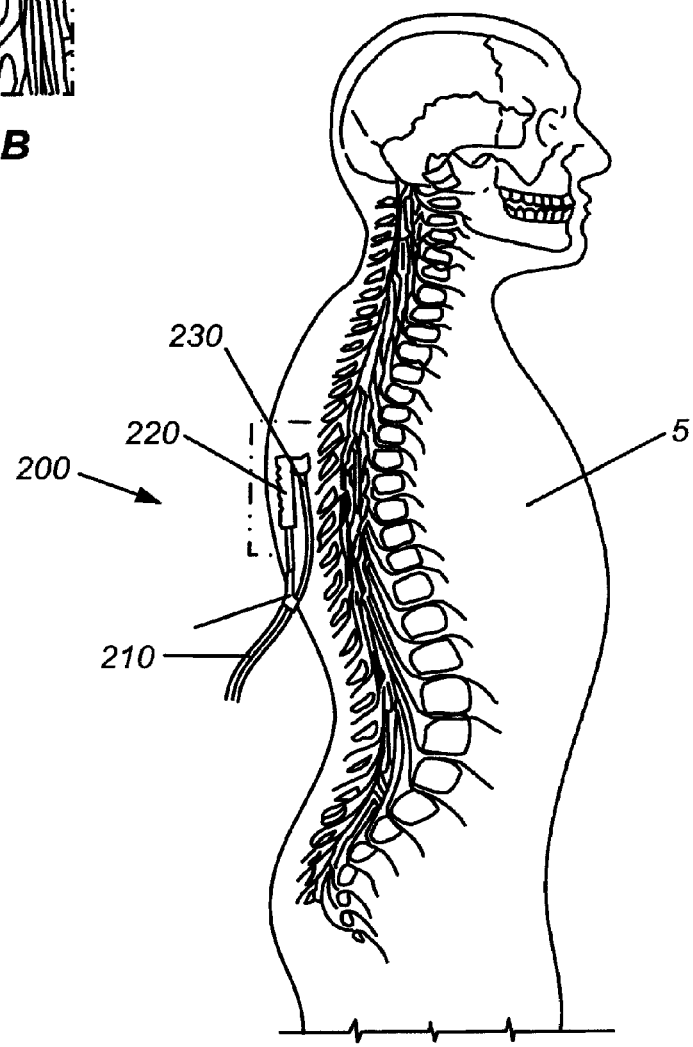
FIG. 14A illustrates a fluid delivery device with a withdrawal member in use.

FIG. 14A illustrates a device 200 with a planar delivery member 220 and one withdrawal member 230 positioned in proximity to the thoracic region of the spinal cord, also viewed through a sagittal plane of the body. The delivery member 220 and a portion of the tubular body 210, as well as the withdrawal member 230 are positioned in the body cavity 5. A portion of the tubular body 210 and the withdrawal member 230 are positioned exterior to the body cavity where they communicate with a fluid reservoir and a disposal reservoir. FIG. 14B is a close-up view of the device 200 positioned in the body cavity illustrating the outflow of fluid from the delivery member 220 and the inflow of fluid into the fenestrations 238 of the withdrawal member 230. The delivery member 220 is positioned dorsally, or exteriorly, to the withdrawal member 230, which is positioned dorsally to the target tissue. This positioning facilitates removal of excess fluid delivered from the delivery member prior to the fluid reaching the target tissue.

Figure 15A:
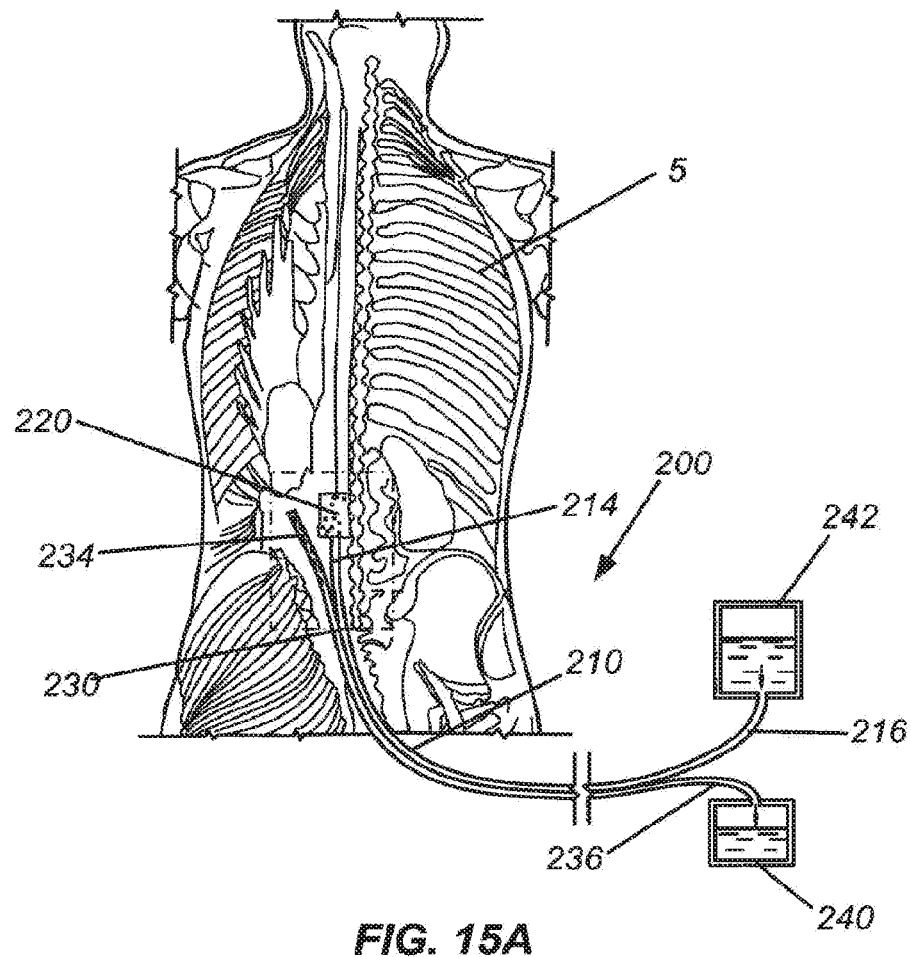
FIG. 15A illustrates a fluid delivery device withdrawal element in use as viewed from the posterior.
Figure 15B:
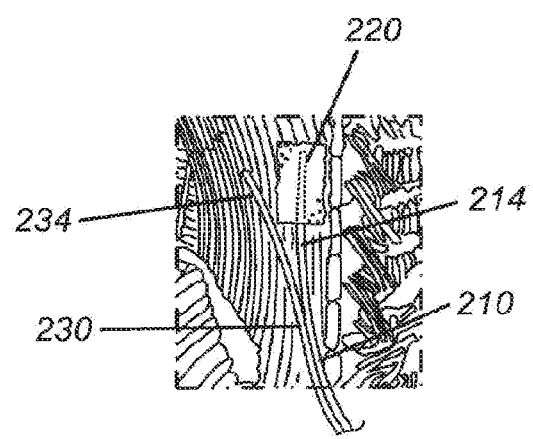
FIG. 15B is a close-up view of the fluid delivery device in use.

FIG. 15A illustrates a device 200 in position within the body cavity 50 as viewed from the posterior side of the patient. The device is positioned such that the planar delivery member is positioned to provide its largest surface area largely within a coronal plane. The delivery member 220 and distal end 214 of the tubular body 210 are positioned adjacent to the musculature surrounding the lumbar region of the spinal cord. The proximal end 216 of the tubular body 210 is in fluid communication with a fluid reservoir 242. The distal end 234 of a withdrawal member 230 is positioned to the left of the delivery member 220 as viewed from the posterior side of the patient. The proximal end 236 of the withdrawal 230 member is located outside of the body cavity 5 and is in fluid communication with a disposal reservoir 244. FIG. 15B is a close-up view of the distal ends 214, 234 of the tubular body 210 and withdrawal member 230, respectively.

Figure 16:
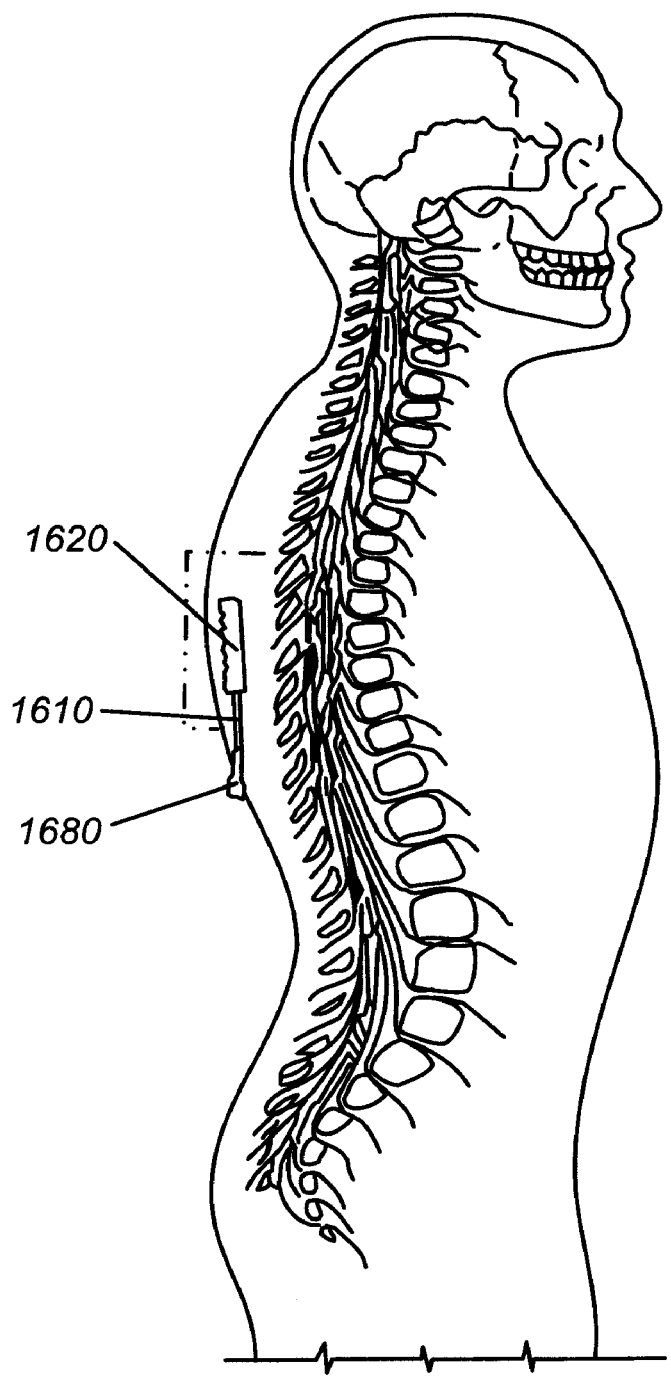
FIG. 16 is an illustration of a fluid delivery device in use with a port reservoir.

FIG. 16 illustrates a device 1600 that employs the use of a port 1680 attached to the delivery device 1620 through the tubular body 1610 through a coronal plane of the body. The port 1680 can be attached directly to the patient through any suitable mechanism for adhering the port to the patient, such as through the use of tape, glue, bandages, gauze, or any other suitable mechanism for adhering the port. The port 1680 is filled with fluid and the fluid is delivered to the anatomical region through the tubular body 1610 and delivery member 1620, of which the proximal end 1616 of the tubular body 1610 is in fluid communication with the port 1680. The port can be refilled when empty, and can be refilled with the same fluid being used during the first administration of fluid. Alternatively, a first fluid can be administered to the patient through the port 1680 and a second fluid administered to the patient through the port 1680 after the administration of the first fluid is completed. The port serves as a portable reservoir for the device 1600.

II. METHODS

Figure 17:
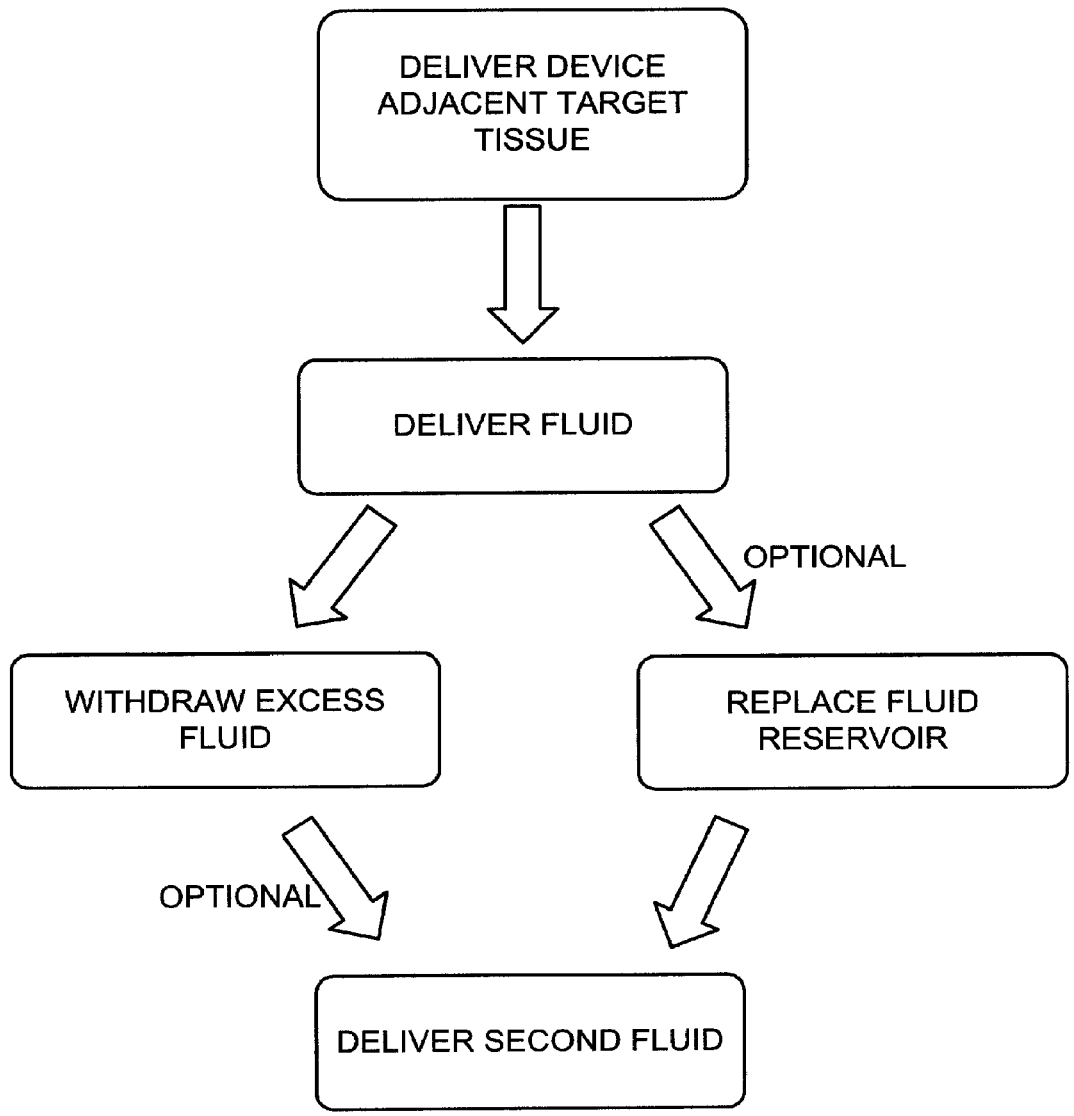
FIG. 17 is a flow diagram of the method of use of a fluid delivery device.

A variety of methods are also contemplated, one of which is illustrated in FIG. 17. One method includes a method for delivering a fluid to a subject. The method comprises: delivering a distally positioned delivery member adjacent a target tissue within a mammalian body; delivering fluid to the delivery member via an elongate tubular body; and withdrawing excess delivered fluid adjacent the target tissue via a withdrawal member. The target tissue can be tissue selected from spinal dura mater, skin, subcutaneous tissue, paraspinal muscle, bone, ligaments, facia, and neural elements. The method can further comprise the step of detaching the delivery member from the tubular body. Additionally, the method may include the step of applying a vacuum to the delivery member. The distal portion of the delivery member can be removed after a therapeutic length of time has elapsed. The fluid used could be a medicament comprising one or more of anesthesia, anti-inflammatories, analgesics, anti-catabolites, growth factors, hormones, or any viral/recombinant proteins. Additionally, the step of replacing the first reservoir with a second reservoir may be used. A first fluid can be delivered through via the first reservoir and a second fluid can be delivered via the second reservoir. The method can further include the step of positioning the device extradurally, subfascially, subcutaneously, percutaneously, or intramuscularly. Additionally, the delivery of fluids can be controlled or adjusted in response to measuring a target parameter of the patient.

III. KITS

A variety of kits are also contemplated. For example a kit for administering fluid can be provided comprising, for example, (a) an elongate body defining a lumen throughout a portion thereof, a distal end interiorly positionable adjacent the anatomical region of the mammal and a proximal end in communication with an exterior of the mammal; (b) a delivery member having an exterior surface, and (c) a withdrawal member. The kit may further comprise a delivery reservoir in communication with the delivery member. A sensor in communication with the delivery reservoir and a controller adapted to control the rate at which fluid is delivered may also be included. Additionally, the kit may further comprise a disposal reservoir in communication with the withdrawal member.

A drug delivery kit is also contemplated. A drug delivery kit could comprise, for example, (a) a delivery tube for delivering a fluid to a local area of tissue, (b) a diffuser in fluid communication with the delivery tube, wherein the diffuser is adapted to be sized to the area of tissue, and (c) a drainage tube for removing fluid from the local area of tissue. The kit may further comprise a fluid reservoir. Additionally, the kit may include a suction device, wherein the suction device applies reduced pressure to the area of tissue through the drainage tube.

A kit comprising a device for delivering fluid to an anatomical region of a mammal is also contemplated comprising, for example, (a) an elongate body defining a lumen throughout a portion thereof, a distal end interiorly positionable adjacent the anatomical region of the mammal and a proximal end in communication with an exterior of the mammal, and (b) a distally positioned non-tubular delivery member having an exterior surface. In some embodiments, the kit may include a withdrawal member and may include more than one withdrawal members. A delivery reservoir may be included in the kit wherein the delivery reservoir is in communication with the non-tubular delivery member. Additionally a disposal reservoir in communication with the one or more withdrawal members may be included in the kit.

A kit comprising a device for delivering fluid to an anatomical region of a mammal can alternatively comprise (a) an elongate body defining a lumen throughout a portion thereof, a distal end interiorly positionable adjacent the anatomical region of the mammal and a proximal end in communication with an exterior of the mammal, and (b) a distally positioned delivery member having an exterior surface adapted to deliver fluid from a portion of the exterior surface adjacent the target tissue. In some cases, the kit may further comprise one or more withdrawal members. The kit may further comprise a delivery reservoir in communication with the delivery member. A sensor in communication with the delivery reservoir and a controller adapted to control the rate at which fluid is delivered may also be included. Additionally, the kit may further comprise a disposal reservoir in communication with the withdrawal member.

In an alternative embodiment of a drug delivery kit, the kit may comprise (a) a delivery tube for delivering a fluid to a local area of tissue, and (b) a diffuser in fluid communication with the delivery tube, wherein the diffuser is adapted to be sized to the area of tissue, wherein the fluid is delivered to the local area of tissue through the diffuser. The kit in some embodiments can also include a fluid reservoir for providing fluid to the diffuser through the delivery tube. Additionally, a drainage tube may be included in the kit, wherein the drainage tube is used to remove fluid from the local area of tissue.

VI. EXAMPLES

Example 1

Delivery of Bupivacaine for Postoperative Pain Control after Lumbar Spine Surgery The device can be used to deliver bupicacaine to patients who are scheduled to undergo elective posterior lumber discectomy, or decompressive laminectomy with or without instrumented fusion for degenerative spinal diseases. A device is selected that conforms to the size of the surgical area. The device will be placed in the body cavity in the lumbar region of the spinal cord following surgery and the wound will be bandaged to prevent debris from entering the wound. A solution containing bupivacaine will then be administered at the target tissue site in the body cavity for 24 hours following surgery to alleviate pain associated with the surgical procedure. The device will then be removed from the patient and the surgical incision closed following removal.

Example 2

Delivery of Anesthetic at an Iliac Crest Bone Graft Site

The device can also be used to alleviate pain associated with harvesting tissue from an iliac crest bone graft site. Patients undergoing posterior iliac crest bone graft harvesting can be fit with the device described. The device is placed in the body cavity which is fit with a delivery member. A solution of 0.5% Marcain is delivered to the patient for 48 hours following surgery. The delivery member will be chosen of a density so that the rate of infusion is 2 ml/h for the 48 hours. The delivery member and the elongate body are then removed from the patient.

Example 3

Infusion of Levobupivacaine Following Thoracotomy

The device described can also be used to alleviate pain following throacotomy. Patients undergoing surgical procedures requiring access to the thoracic region of the body, such as cardiothoracic surgery. The elongate tube and delivery member can be inserted in the body cavity before induction of anaesthesia and a loading dose of levobupivacaine administered. At the end of surgery, the levobupivacaine can continue to be administered at 5 ml/h for 48 hours. After 48 hours the elongate body is detached from the delivery member. The patient is then closed. The delivery member, infused with the levobupivacaine, continues to administer additional levobupivacaine to the surgical area. The delivery member is then resorbed by the body over time.

Example 4

Delivery of Morphine and Neostigmine for Postoperative Analgesia after Orthopedic Surgery The device can be used to administer analgesics to anatomical regions following orthopedic surgery. Patients undergoing knee surgery can be fit with a device in which the withdrawal element is nested within a spiral cut elongate tube. A combination of morphine and neostigmine is then administered to the surgical site through the spiral cuts of the elongate body. Excess fluid surrounding the joint is then removed through the fenestrations in the withdrawal member. The combination of morphine and neostigmine will be administered for up to 72 hours as needed by the patient. The device is then removed following administration of fluid and the surgical site closed.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of post-surgical pain relief to tissues adjacent a surgical wound, the method comprising:
    performing a surgical procedure creating a surgical wound;
    providing a catheter assembly comprising:
        an elongated catheter having a proximal supply end extendable outwardly from a patient, a distal delivery end and an external wall defining an internal lumen extending from the proximal supply end to the distal delivery end, the distal delivery end including at least one opening communicating from the internal lumen to an environment surrounding the elongated catheter, the distal delivery end having a width dimension; and
        a delivery member in fluid communication with the at least one opening, the delivery member having a generally planar configuration with a length dimension, a width dimension perpendicular to the length dimension, and a depth dimension perpendicular to the length dimension and the width dimension, the length and width dimensions being greater than the depth dimension, the width dimension of the delivery member being greater than the width dimension of the distal delivery end of the elongated catheter, the delivery member having at least a first porous surface and a second non-porous surface, wherein the first porous surface and the second non-porous surface are opposite one another;
    placing the delivery member of the catheter assembly adjacent the surgical wound with the first porous surface of the delivery member adjacent the tissues to be treated for post-surgical pain, and with the second non-porous surface facing nerves adjacent the surgical wound; and passing pain relieving medication through the elongated catheter, through the at least one opening, and through the first porous surface to diffuse the pain relieving medication over an area of the tissues to be treated while the pain relieving medication is blocked from passing through the second non-porous surface so as to provide post-surgical pain relief in a constrained configuration to tissues adjacent the surgical wound while preventing diffusion of the medication over a given area of diffusion to the nerves adjacent the surgical wound.

2. The method of claim 1 further comprising positioning a drain in the surgical wound, applying suction to the drain, and withdrawing fluids from the surgical wound.

3. The method of claim 1 further comprising:

positioning a sensor in the wound;

sensing a wound parameter; and controlling the flow of pain relieving medication to the wound in response to the sensed parameter.

4. The method of claim 1 further comprising separating the delivery member from the catheter and closing the wound with the delivery member implanted within the patient.

5. The method of claim 2 wherein the drain is separated from the first porous surface by the second non-porous surface.

6. The method of claim 5 wherein the surgical procedure is a posterior spinal surgical procedure and the tissues to be treated are tissues of the patient's back.

7. The method of claim 1 wherein the delivery member is bioresorbable.

8. The method of claim 1 wherein the delivery member is a sponge.

9. The method of claim 1 wherein the delivery member comprises a fibrous structure.

10. The method of claim 1 wherein the surgical wound comprises a surgical wound of a spinal surgical procedure, the nerves are spinal nerves, the tissues to be treated for post-surgical pain are tissues opposite the spinal nerves, the non-porous surface is oriented toward the spinal nerves and the porous surface is oriented toward the tissues to be treated for post-surgical pain.

11. The method of claim 2 wherein positioning the drain in the surgical wound includes positioning the delivery member between the drain and the nerves.

* * * * *